(12) United States Patent
Wells et al.

(10) Patent No.: US 10,286,128 B2
(45) Date of Patent: May 14, 2019

(54) PRESSURE CONTROL DURING PROCESSING OF ADIPOSE TISSUE

(71) Applicants: John F. Wells, Tucson, AZ (US); McKay S. Crowder, Tucson, AZ (US)

(72) Inventors: John F. Wells, Tucson, AZ (US); McKay S. Crowder, Tucson, AZ (US)

(73) Assignee: WELLS JOHNSON COMPANY, Tucson, AZ (US)

( * ) Notice: Subject to any disclaimer, the term of this patent is extended or adjusted under 35 U.S.C. 154(b) by 0 days.

(21) Appl. No.: 16/183,263

(22) Filed: Nov. 7, 2018

(65) Prior Publication Data

US 2019/0091386 A1    Mar. 28, 2019

Related U.S. Application Data

(63) Continuation-in-part of application No. 15/647,736, filed on Jul. 12, 2017, now Pat. No. 10,143,811, (Continued)

(51) Int. Cl.
*A61M 31/00* (2006.01)
*A61M 1/00* (2006.01)
(Continued)

(52) U.S. Cl.
CPC ...... *A61M 1/0084* (2013.01); *A61M 5/14232* (2013.01); *A61M 5/158* (2013.01);
(Continued)

(58) Field of Classification Search
CPC .......... A61M 5/178; A61M 5/30; A61M 5/20; A61M 5/142; A61M 5/16831;
(Continued)

(56) References Cited

U.S. PATENT DOCUMENTS 5,813,842 A * 9/1998 Tamari ................ A61M 1/3621
417/477.1
2009/0269315 A1* 10/2009 Fraser ................ A61L 27/3834
424/93.7

(Continued)

*Primary Examiner* — Jason E Flick
(74) *Attorney, Agent, or Firm* — Yakov S. Sidorin; Quarles & Brady LLP

(57) ABSTRACT

An adipose tissue (AT) transfer system includes, on the aspiration side, an aspiration cannula, an aspiration pump, a container, and flexible tubing connecting the aspiration cannula to the container. On the reinjection side, the system includes a reinjection cannula, flexible tubing connecting the inlet of the reinjection cannula to the container, and a reinjection pump imposing positive-displacement pumping action on the flexible tubing and causing movement of AT in a continuous or pulsed mode. The aspiration pump operates to continually supply harvested AT to the second flexible tubing while the reinjection pumps causes continuous or pulsed deposition of the AT at the injection site. To ensure that internal pressure and/or flow of the AT through a channel of delivery of the AT to the reinjection site does not exceed a predetermined value, defined with respect to pressure causing rupture of a blood-vessel at the recipient site, the system contains an external pressure sensor configured to measure such internal pressure in absence of a part that is in direct contact with the AT.

20 Claims, 16 Drawing Sheets

Related U.S. Application Data which is a continuation-in-part of application No. 15/160,818, filed on May 20, 2016, now abandoned, application No. 16/183,263, which is a continuation-in-part of application No. 15/649,118, filed on Jul. 13, 2017, now Pat. No. 10,130,740, which is a continuation-in-part of application No. 15/160,818, filed on May 20, 2016, now abandoned.

(60) Provisional application No. 62/179,885, filed on May 22, 2015.

(51) Int. Cl.
  *A61M 5/142* (2006.01)
  *A61M 5/158* (2006.01)

(52) U.S. Cl.
  CPC . *A61M 2202/08* (2013.01); *A61M 2205/3344* (2013.01); *A61M 2205/50* (2013.01); *A61M 2205/505* (2013.01)

(58) Field of Classification Search
  CPC .. A61M 5/1723; A61M 1/0058; A61M 31/00; A61M 5/16877; A61M 5/16881; A61M 5/1424; A61M 5/158; A61M 2202/08; A61M 2202/09; A61M 2205/33; A61M 2205/3327; A61M 2205/3331; A61M 2205/3344; A61M 2205/3351; A61M 2205/3355
  USPC .......................................................... 604/66
  See application file for complete search history.

(56) References Cited

U.S. PATENT DOCUMENTS

| | | | |
|---|---|---|---|
| 2010/0204765 A1* | 8/2010 | Hall | A61F 7/12 607/105 |
| 2013/0035660 A1* | 2/2013 | Anand | A61M 5/16804 604/500 |
| 2014/0228755 A1* | 8/2014 | Darrah | A61M 5/155 604/113 |
| 2016/0361476 A1* | 12/2016 | Huang | C12M 45/02 |

* cited by examiner

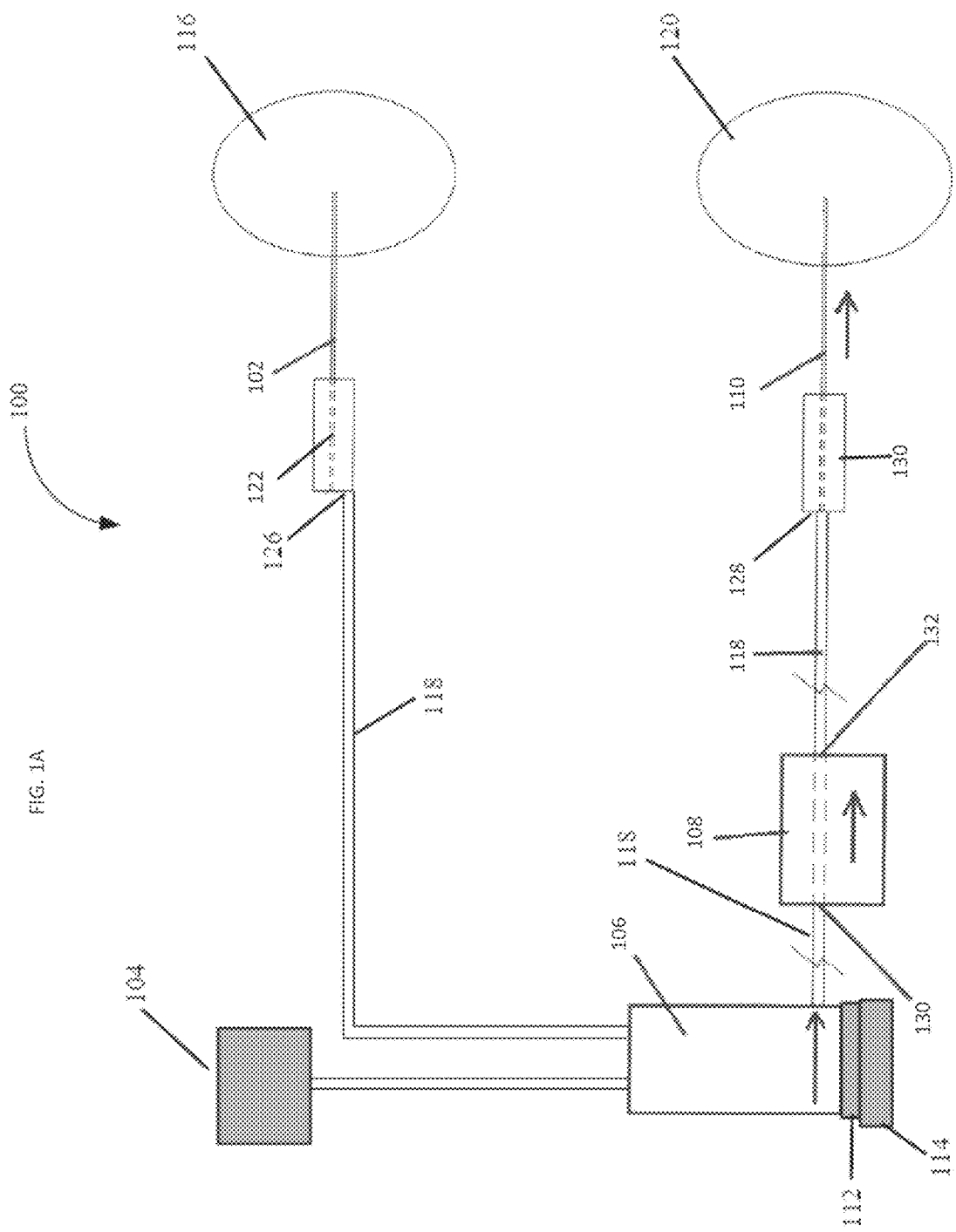

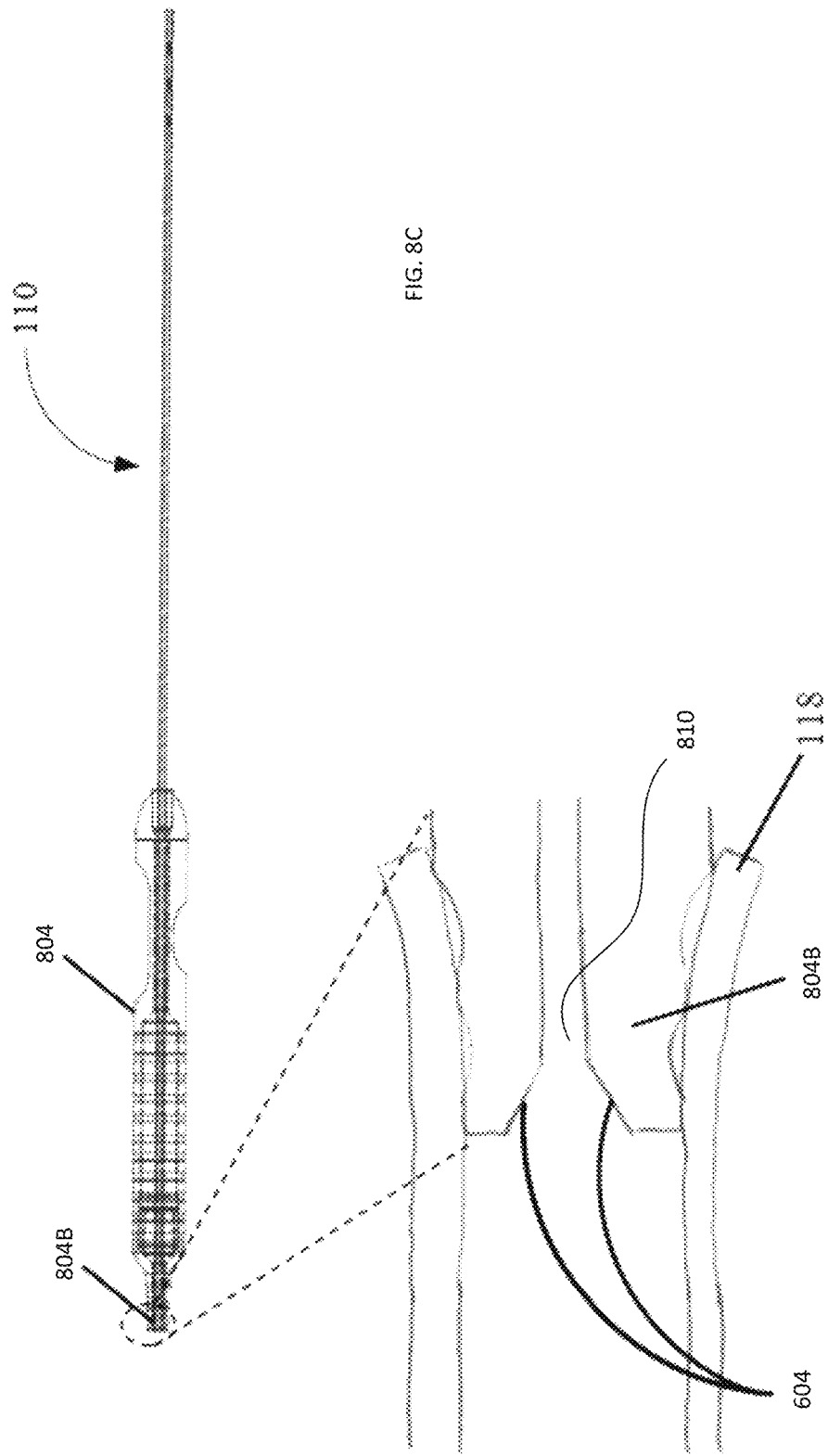

Clamp Testing For Best Fit Curve

| Initials | MC | Date | | Time | 11:00 AM |
|---|---|---|---|---|---|

| | | | Tubing | Standard Soft PVC from ARMM |
|---|---|---|---|---|
| HVP Unit | 5 | | | |
| Load Cell | 1 | | | |
| Clamp Number | 1p | | | |
| Zero Clamp Reading | 519 | mV | | |

| | | Test Number | | | | | |
|---|---|---|---|---|---|---|---|
| | PSI | 1 | 2 | 3 | 4 | 5 | 6 |
| Initial Starting Output | 0 | 796 | 763 | 781 | 755 | 755 | 732 |
| Output of Clamp, 2psi | 2 | 832 | 806 | 815 | 794 | 791 | 777 |
| Output of Clamp, 4psi | 4 | 844 | 828 | 837 | 818 | 810 | 797 |
| Output of Clamp, 6psi | 6 | 865 | 855 | 860 | 850 | 841 | 827 |
| Output of Clamp, 8psi | 8 | 889 | 876 | 890 | 881 | 866 | 855 |
| Output of Clamp, 10psi | 10 | 918 | 917 | 918 | 915 | 897 | 884 |
| Output of Clamp, 12psi | 12 | 950 | 954 | 952 | 950 | 928 | 922 |
| Output of Clamp, 13psi | 13 | 974 | | 970 | 967 | 939 | 946 |

| RPM | 50 |
|---|---|

Notes: * = did not return to zero pressure reading
** = slow return to zero, up to 10 sec
NOTES: Test 1: Clamp on tube, run test immediately. Test 2: do not touch clamp and re-run test 1. Test 3: move clamp and reclamp, test immediately. Test 4: do not touch clamp and re-run test 3. Test 5: move clamp and re-clamp. Test Immediately. Test 6: did not touch clamp, re-run test 5

FIG. 12A

PRESSURE CONTROL DURING PROCESSING OF ADIPOSE TISSUE

CROSS-REFERENCE TO RELATED APPLICATIONS

The present application a continuation-in-part from the U.S. patent application Ser. No. 15/647,736 filed on Jul. 12, 2017 and now published as US 2017/0348493, which is in turn a continuation-in-part from the U.S. Ser. No. 15/160,818 filed on May 20, 2016, which in turn claims priority from the U.S. Provisional Patent Application No. 62/179,885 filed on May 22, 2015.

The present application is also a continuation-in-part from the U.S. patent application Ser. No. 15/649,118 filed on Jul. 13, 2017 and now published as US 2017/0304509, which is in turn a continuation-in-part from the U.S. Ser. No. 15/160,818 filed on May 20, 2016.

The disclosure of each of the above-identified patent applications is incorporated by reference herein.

TECHNICAL FIELD

This invention is related in general to systems, processes, and methods of harvesting and reinjecting adipose tissue. In particular, the invention pertains to a method and system for controlling the level of tissue-reinjection pressure and/or the tissue-flow rate and adjusting, in real-time, such pressure and/or rates (based on acquired empirical knowledge of consequences of such control) in order to continually maintain the safety and/or structural integrity of the patient's recipient site.

BACKGROUND

Liposuction procedures have gained popularity, and more recently there has been an increase in industry demand for reinjecting the adipose fat tissue (that has been harvested or removed from one bodily part) to another bodily part. While such reinjection procedures are currently moderately successful in terms of completion, no attention has been paid to-date to the question of preventing build-up of pressure of the biological fluid (including the adipose tissue) not only during the propagation through the system used for transfer of such biological fluid from the initial location (or source, for short, such as a container or even the location of harvesting of the adipose tissue) to the final location (or target location, such as for example the reinjection site) but, more importantly, at the target location itself while the fluid is being delivered and injected there. The issue of lack of real-time control of pressure build up raises not only the question of whether the viability of the biological fluid (in this example—the adipose tissue) upon its transfer through the system and the re-injection is maintained or not: such problem was addressed in our prior applications. The lack of real-time pressure control and adjustment begs a more critical question of whether or not the patient (the biological tissue at the target location) becomes distressed or is exposed to injury as a result of delivery of the biological fluid under possibly over-pressurized conditions. And that is all despite the reports in related art that detrimental effects of reinjection of adipose tissue (and even effects leading to extreme consequences) continue to accompany the adipose tissue reinjection in such a common-procedure circumstances as, for example, gluteal fat grafting. Instead, the industry and related art continue to focus on minimization of time required to complete a procedure under the circumstances that seemingly allow maintaining patient's safety.

A person of skill in the art would readily recognize that between these two questions, which are currently of interest to the industry, the one of the ability to keep the site-recipient of the biological fluid reinjection safe during the reinjection procedure is arguably more critical, because in absence of the assurance of a real-time adjustment of the procedure as a function of pressure in the delivery channel, such procedure is, at a minimum, detrimental to the patient, and should be avoided. Understandably, keeping the patient safe upon the reinjection of the AT should be viewed as priority regardless of whether the viability of the fluid/AT (extracted from the aspiration site at pressures preferably not exceeding negative 1 atmosphere to ensure the viability of the AT upon aspiration) is maintained or preserved upon its reinjection.

The present disclosure addresses the question of decisive importance to the fat grafting industry—the active, real-time control of pressure at which the adipose tissue is being transferred to the target location during the reinjection procedure and, in fact, immediate interruption and cessation of the bodily fluid grafting once the pre-determined pressure threshold is reached to prevent detrimental influence on the recipient biological tissue.

SUMMARY

Embodiments of the invention provide a method for adipose tissue (AT) transfer from a source of the AT to a recipient site. Such method includes channeling the AT (within a hollow of a delivery channel of the AT transfer system) from a first end of the delivery channel to a second end of the delivery channel, the second end being placed at the recipient site; and during such channeling, measuring at least one of (i) internal pressure formed by the AT within the hollow and (ii) a change in the internal pressure. The method also includes a step of modifying a parameter of said channeling once said internal pressure exceeds a pre-determined threshold that is defined based at least in part on a pressure level causing rupture of a wall of a blood-vessel at the recipient site. Generally, the pre-determined pressure level is dependent on a location of the reinjection site in a human body.

In one specific implementation, the pre-determined threshold is substantially equal to pressure exceeding a modulus of a practical aspiration pressure, as defined herein, by no more than 1.21 atmosphere. IN another related specific implementation, the pre-determined threshold is defined within a range from a first pressure level to a second pressure level, the first pressure level exceeding a modulus of a practical aspiration pressure by no less than 0.13 atmosphere, the second pressure level exceeding the practical aspiration pressure by no more than 3.3 atmosphere. In yet another specific implementation, the pre-determined threshold is defined within a range from a first pressure level to a second pressure level, the first pressure level exceeding a modulus of a practical aspiration pressure by no less than 1.21 atmosphere, the second pressure level exceeding the practical aspiration pressure by no more than 1.8 atmosphere.

Alternatively or in addition, the process of channeling may include transferring the AT through a first flexible tube having a first inner diameter and through a second flexible tube having a second inner diameter, the first and second diameters being substantially equal. Alternatively or in addition, the method may additionally comprise conveying the AT through an aspiration cannula of the AT transfer system under first pressure, where the channeling includes channeling the AT under second pressure, a modulus of a value of the second pressure not exceeding the pre-determined threshold. Alternatively or in addition, the process of channeling may include forming a first area of first internal pressure and a second area of second internal pressure in the hollow, the first internal pressure being higher than internal pressure present in the hollow at the first end, the second internal pressure being lower than the internal pressure present in the hollow at the second end. Alternatively or in addition, the method satisfies at least one of the following conditions: (i) the measuring is devoid of establishing physical contact between a component of the pressure sensor and the AT being channeled within the hollow; (ii) the measuring includes generating an electrical signal in response to a change of a geometrical parameter of the delivery channel, where the change caused by a change of the internal pressure; and iii) the measuring includes generating indicia of the internal pressure exceeding the pre-determined threshold at a location of a first side-wall opening of a reinjection cannula of the transfer system, the reinjection cannula having been inserted into the recipient site. In a specific implementation of the latter case, the indicia includes an electrical signal, and the process of modifying includes modifying a parameter of operation of a reinjection pump of the AT transfer system, where the reinjection pump being operably attached to the delivery channel.

In a particular case, the modifying includes stopping a motor of a reinjection pump of the AT transfer system or even reversing a direction of AT pumping until the internal pressure is reduced to substantially zero. In a particular case, the first end includes a side-wall opening of an aspiration cannula of the AT transfer system, the second ends includes a side-wall opening of a reinjection cannula of the transfer system, and the process of channeling includes extracting the AT from an aspiration site and collecting the AT in a container in fluid communication with both the aspiration and reinjection cannulae. In yet another related embodiment, the method includes at least one of the following steps: (a) injecting the AT through the second end into the recipient site in a pulsed fashion; and (b) injecting the AT into the recipient site through a first side-wall opening of a reinjection cannula of the system while the AT is being harvested from an aspiration site through a second side-wall opening of an aspiration cannula of the system, where the aspiration cannula and the reinjection cannula are uninterruptingly fluidly connected during said channeling.

Embodiments of the invention also provide a system configured to deliver an adipose tissue to a recipient site. Such system includes: a biocompatible flexible tubing with a first end and a second end (where the first end is dimensioned to receive said adipose tissue that has been received from a source location, and the second end in operation is fluidly connected to a location of the recipient site); a first pump attached to the flexible tubing to cause movement of adipose tissue through the flexible tubing from the first end to the second end; a pressure sensor operably connected to at least one of the first pump and the flexible tubing to measure an internal pressure of the adipose tissue upon its propagating through the flexible tubing; and a reinjection cannula fluidly connected to the second end. Here, the pressure sensor is configured to cause the system to interrupt a process of propagation of the adipose tissue through the flexible tubing to prevent fat embolism at the recipient site when pressure of the adipose tissue at a side-wall opening of the reinjection cannula exceeds a predetermined amount.

Here, the predetermined amount is dependent on the location of the recipient site in a human body while, at the same time, the predetermined amount is defined based at least in part on a pressure level causing rupture of a wall of a blood-vessel at the recipient site.

In one embodiment, the predetermined amount is defined within a range of pressure levels from a first pressure level to a second pressure level, wherein the first pressure level exceeds a modulus of a practical aspiration pressure by no less than 0.13 atmosphere and the second pressure level exceeds the practical aspiration pressure by no more than 3.3 atmosphere.

In a related embodiment, the pressure sensor is configured to cause the system to interrupt the process of propagation of the adipose tissue through the flexible tubing when pressure of the adipose tissue at the side-wall opening of the reinjection cannula exceeds a modulus of practical aspiration pressure by more than 1.21 atmosphere. In another related embodiment, the predetermined amount is defined within a range of pressure levels from a first pressure level to a second pressure level, wherein the first pressure level exceeds a modulus of a practical aspiration pressure by no less than 1.21 atmosphere and the second pressure level exceeds the practical aspiration pressure by no more than 1.8 atmosphere.

Optionally, the first pump is devoid of a portion that, in operation, contacts the adipose tissue in the flexible tubing and/or the pressure sensor is devoid of a portion that, in operation, contacts the adipose tissue. The flexible tubing may be configured to have, in absence of external force applied to the flexible tubing, a substantially constant internal diameter at any point between the first and second ends.

Depending on the implementations, (i) the first pump may include a first pump controller configured to operate the first pump in a pulsed regime to cause the adipose tissue move in a pulsed fashion from the first end to the second end; and/or (ii) the pressure sensor may include a transducer configured to measure the internal pressure by measuring a change of a parameter of the flexible tubing caused by changes in the internal pressure; and/or the first pump may be devoid of a movable part that is internal to the flexible tubing. A particular implementation of the system may include an aspiration cannula and a volume fillable, during an operation of the system, with the adipose tissue, where the volume is disposed in fluid communication between the aspiration cannula and the flexible tubing.

Embodiments of the invention additionally provide a system configured to deliver an adipose tissue to a recipient site, which system includes: a storage volume containing the adipose tissue; a hollow delivery channel with first and second ends, the first end fluidly connected with the storage volume, the second end fluidly connected with a location of the recipient site; a first pump configured to apply a positive-displacement pumping force to the delivery channel to cause a movement of the adipose tissue from the first end to the location of the recipient site; a pressure sensor attached externally to a component of the system, the sensor configured to measure an internal pressure of the adipose tissue in the delivery channel and generate an output signal representative of the internal pressure; and a programmable processor operably connected to the pressure sensor and configured to modify an operation of the first pump, to prevent fat embolism at the recipient site, in response to a value of the output signal being in a pre-determined relationship with a threshold value, wherein the threshold value is dependent on the location of the recipient site while, at the same time, the threshold value represents pressure defined based at least in part on a pressure level causing rupture of a wall of a blood-vessel at the recipient site. In one embodiment of such system, the threshold value is established to represent pressure defined within a range of pressure levels from a first pressure level to a second pressure level, wherein the first pressure level exceeds a modulus of a practical aspiration pressure by no less than 0.13 atmosphere and the second pressure level exceeds the practical aspiration pressure by no more than 3.3 atmosphere.

BRIEF DESCRIPTION OF THE DRAWINGS

The invention will be more fully understood by referring to the following Detailed Description in conjunction with the generally-not-to-scale Drawings, in which similar elements are indicated with similar numbers and labels and of which:

FIG. 1A is a schematic diagram of an embodiment of the adipose tissue transfer system.

FIGS. 8A, 8B, 8C illustrate embodiments of cannulae for use with a transfer system of FIG. 1A according to an embodiment of the invention, including a side view, a cross-sectional side view, and a blown-up cross-sectional side view of an inlet with a tube attached, respectively.

FIGS. 12A, 12B depict an example of results of the system calibration procedure

Figure 1B:
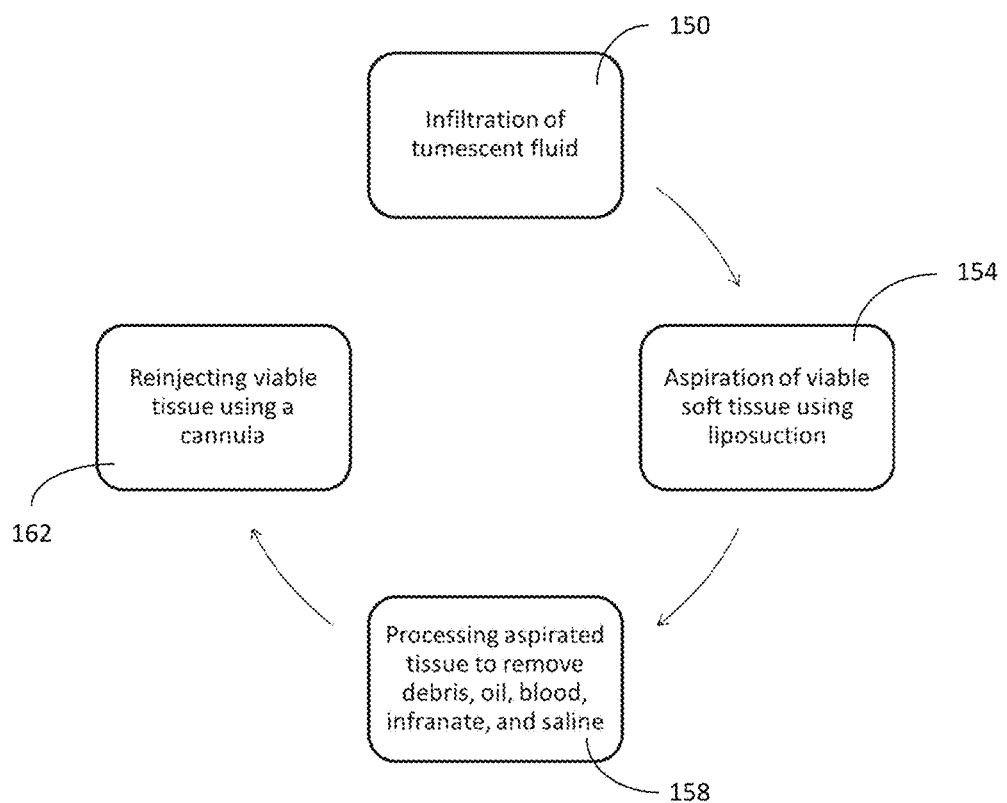
FIG. 1B is a flow-chart showing major steps of conventionally-performed procedure for harvesting and reinjection of adipose tissue.

The sizes and relative scales of elements in Drawings may be set to be different from actual size and scales to appropriately facilitate simplicity, clarity, and understanding of the Drawings. For the same reason, not all elements present in one Drawing may necessarily be shown and/or labeled in another.

DESCRIPTION

The related art leaves unaddressed multiple problems concerning the handling of adipose tissue during the transfer and/or reinjection procedure(s). Related art focuses its attention, with or without substantial success, on the problems of graft survival and/or retention and/or adipose cell viability (see Zielins et al., "Autologous Fat Grafting: The Science Behind the Surgery", Aesthetic Surgery J., 36(4), 488-496, 2016; Strong et al., "The Current State of Fat Crafting: A Review of Harvesting, Processing and Injection Techniques", Plast. Reconstr. Surg. 136: 897, 2015) In considering these topics, the related art appears to side-line the discussion of the patient safety during the reinjection procedure—possibly because this issue evades the attention of the manufacturers of the equipment employed in fat grafting procedure. And yet, understandably, patient safety comes first—there appears to be absolutely no benefit to be derived from the delivery/reinjection of even the perfectly healthy fat cells to the recipient biological tissue that is harmed or killed with such delivery. Accordingly the present invention emphasizes this aspect of the fat adipose tissue (re-)injection procedure: the safety of the biological body into which the adipose tissue is being reinjected.

While a person of skill in the art would now readily appreciate that the viability of the adipose tissue during the process of handling is jeopardized by several factors (such as excessive levels of pressure during the harvesting/reinjection steps, shearing forces, and blunt forces, to name just a few; see for example U.S. Ser. No. 15/649,118), it remains substantially unrecognized by related art that the safety of the recipient of the reinjected adipose tissue also critically depends on the pressure levels at which the adipose tissue is being delivered and reinjected into the target location. In fact, while reporting on statistics of fat embolism during the gluteal fat grafting procedure, related art admits the recurring problem of embolism but addresses it and explains it with the specific aspects of the reinjection procedure—and only provides recommendations to avoid very peculiar elements of the fat grafting such as, for example, fat injections into the deep muscle with the use of cannulae of particular small dimensions (such as cannulae smaller than 4 mm in diameter) and pointing the injection cannula downwards during the reinjection procedure.

The current practice of re-injection of adipose tissue back into a body of the patient and associated methodologies fail to control, monitor, and react in real-time to changes in pressure of the adipose tissue that is being re-injected. And—while the current practices have been shown to have serious implications and often resulted in detrimental injury to the patient—the related art either simply does not recognize the importance of control of pressure during the adipose tissue transfer (advocating, instead, the specific and minute "fixes" of the overall procedure that may, under limited circumstances, alleviate the problem; see for example Mofid et al., in Aesthetic Surgery Journal, pp. 1-11, 2017) or, even expressly asserts that the elimination of high-pressure states during fat transfer is not possible, and that the only certain way to avoid the risk of fat embolism is to avoid venous injury during fat transplantation (see, for example, Vecchio and Wall, in 51st Annual Baker Gordon Educational Symposium, 2017, Florida). Thus, there remains an unaddressed need for a device to effectively manage fluid pressure, in real-time, in both the re-injection system itself and the body of the patient.

The present invention challenges these negative conclusions of the related art, which unavoidably redirect the attention of a skill artisan away from addressing the pressure-caused problems, and provides an adipose tissue transfer equipped with an external control unit configured to generate indicia of the fluid pressure in the system. Unless expressly defined otherwise, for the purposes of this disclosure and accompanying claims a real-time performance of a system is understood as performance which is subject to operational deadlines from a given event to a system's response to that event. For example, a real-time adjustment of pressure caused by the adipose tissue during the process of transfer of such tissue to the recipient site may be one triggered by the processor-controlled system (based on the feedback signal from the pressure-measuring means) and executed simultaneously with the process of adipose tissue transfer during which such feedback signal has been generated while resulting in a change of the process of the operation of the system.

Upon reading the disclosure, a skilled artisan will readily appreciate that avoiding such very specific circumstances does not—and simply cannot—address a much more general problem of embolism during the injection procedure. Clearly, adipose tissue reinjection is not limited to deep muscle tissue but includes reinjection into much more sensitive and critical areas (such as, for example, areas around the eyes) and very often does require the use of cannulae that are very small (or needle-like in terms of inner diameter).

Despite the significance of the problem, and multiple metrics used to ascertain the safety of the adipose tissue reinjection procedure, there appears to be no recognition that what is required is a tissue-reinjection system and method that enables a clinician to at least match and control optimal levels of pressure selected during the reinjection procedure and the ability to interrupt the procedure when such levels are exceeded. The present disclosure attests to the empirical findings that the active pressure control overcomes the practical shortcomings of the existing systems, facilitates the reduction and elimination of the fat embolism during the adipose tissue reinjection and, therefore, ensures not only the safety of the patient but also the viability of the reinjected tissue.

The present invention provides solutions to the problem of ensuring the safety of the target location (the biological tissue that receives the adipose tissue during the reinjection procedure) by including pressure and/or flow-rate control(s) in an operationally closed system such as to stop the reinjection procedure once the pressure level at the recipient site exceeds a predetermined threshold value that is defined, at least in part, by the integrity of blood vessels at the reinjection site.

The un-addressed critical problem of maintaining the patient (recipient site) unharmed during the handling (harvesting and reinjection) of the adipose tissue procedure is solved by configuring an automatic fluid-management system of the invention to control the levels of tissue-reinjection pressure and/or the tissue-flow rates to ensure that the pressure levels at the reinjection site and/or in the channel of delivery of the adipose tissue (reinjection channel) from the source to the recipient site do not exceed at any point at least the levels of pressure at which blood vessels are compromised. This includes the configurations that prevent the transfer system from being clogged with the adipose tissue (which clogging immediately increases the internal pressure).

According to an idea of the invention, while configuring the biological fluid transfer system to achieve these goals, the embodiment of the system according to the invention can be made operationally-closed in that, in a specific implementation, the reinjection of the extracted adipose tissue into the targeted bodily part occurs during the same, temporally-uninterrupted real time process cycle or step or procedure that includes the removing/extraction of the material from the source bodily part. The configuration of the system advantageously avoids the use of and is devoid of a valve in contraptions that are utilized to push/pull the tissue through the path dedicated for transfer of the tissue from the site of harvesting to the site of reinjection. The configuration of the system also takes care of utilizing the tubing and/or hollow channels that, in their normal unchanged state, is characterized by a substantially constant value of inner diameter to transfer the tissue (that is, the tubing that is devoid of changes in corresponding diameter value while it is initial, unaffected by the external influence state).

Furthermore, the system is configured to enable a reinjection of the tissue in a pulsed mode, when required, to address the need in spatially-uniform distribution of reinjected tissue across the target (reinjection) site, to provide the reinjected tissue with spatially-even supply of blood.

In one implementation, such external control unit includes a pressure sensor operably associated with the transfer channel(s) (tubing, for example) along which the harvested adipose tissue is being delivered to the injection site. The pressure sensor may be cooperated with the system at the system's pump or engine or, for example, as an in-line sensor (in a specific case—an external pressure sensor). To ensure that the adipose tissue is transferred in a completely sterile fashion, the pressure sensor may be configured to operate by way of clamping to the outside of the channel(s) tubing (that internally channels the adipose tissue) with a transducer (one version of which may employ a load cell), thereby completely eliminating the need to make any direct contacts with the fluid/adipose tissue being transferred through the channels/tubing. The control unit is configured to be in operable communication with the control mechanism that provides power to the pump used to push the adipose tissue into the injection site. An unacceptable rise in pressure in the tubing (which correlates to a rise in pressure in either (or both) the system itself and at the injection site) is advantageously employed to cause the reinjection pump to cease delivery of the adipose tissue, thereby effectively and unprecedently increasing patient safety.

For the purposes of this disclosure, and unless specifically defined otherwise, the term "positive displacement pump" refers to a pump with an expanding cavity on the suction side and a decreasing cavity on the discharge side. For example, during the use of a positive pressure pump, such as a peristaltic pump, liquid is caused to flow into the pump as the cavity on the suction side expands and to flow out of the discharge as the cavity collapses. The term "internal pressure" is used to refer to a measure of force exerted on the interior structure of a closed system. For example, the internal pressure of a flexible tube is the force exerted on the inside walls of the tube by the fluid or gas that is contained within the tube.

Examples of a Transfer System

FIG. 1A provides a schematic diagram of a system of the invention, in which not every component or element of the system is necessarily shown, for simplicity of illustration. The schematic diagram illustrates a harvesting and reinjection system (transfer system) 100 that includes an aspiration cannula 102, a source of vacuum 104, a fatty tissue harvesting container 106, a reinjection pump 108, and a reinjection cannula 110, all connected in a fluidly-uninterrupted transfer channel of the system 100. Additionally, a specific implementation of the system of the invention may include a scale 112, and a vibrating support or table 114.

Generally, harvesting and reinjection procedure of viable soft tissue includes several different steps, among which are (as schematically illustrated in FIG. 1B): infiltration of tumescent fluid, at 150; aspiration of viable soft tissue using liposuction, at 154; processing aspirated tissue to remove debris, oil, blood, infranate, and saline, at 158; and reinjection of viable tissue using a reinjection cannula, at 162.

For better understanding of the transfer system 100, a digression may be in order to outline some features of the cannulae of the system. To this end, features of atypical cannulae used on the aspiration (harvesting) side and the reinjection side of the system of the invention are discussed in reference to FIGS. 8A, 8B, 9A, 9B, 10A, 10B, and 10C.

Embodiments of Cannulae

Figure 8A:
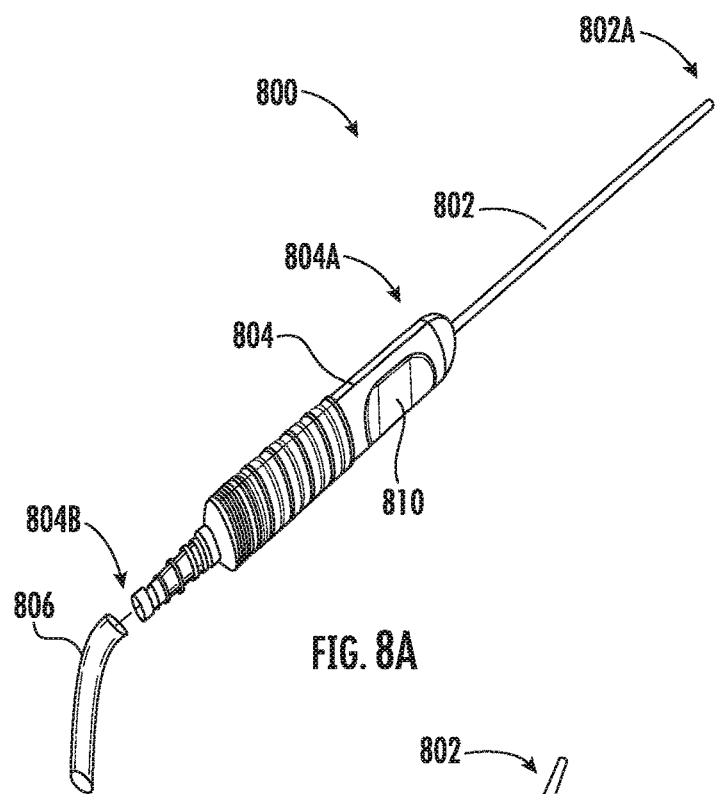
Figure 8B:
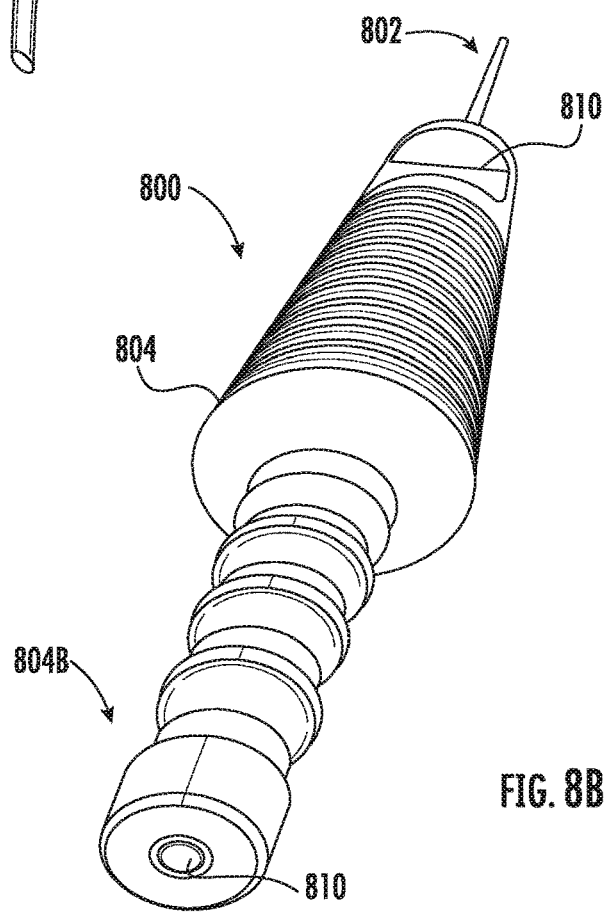

Unless expressly defined otherwise, the terms "cannula", "cannulae" and similar terms are used in this disclosure to refer to a narrow tubular element (whether substantially rigid or flexible) configured for insertion into a tissue to deliver to the tissue or remove from the tissue a predetermined material. In one example, the cannula is configured as a metallic tubular element insertable into the biological tissue for removal ("harvesting") or delivery ("injection"/"reinjection") of adipose tissue. (The latter is known to be a type of connective tissue containing tissue resembling fat, and adipose cells, which are specialized to produce and store large fat globules.) A schematic diagram of a unit 800 containing a cannula 802, fluidly connected to a distal end 804A of a handle or handle grip 804 and further to the typically flexible tubing 806 (for example, silicone or rubber tubing) is shown in FIG. 8A (the tubing 806 is indicated to be dis-attached from the barbed or ribbed proximal end 804B of the handle, for illustration purposes only). The distal end 802A of the cannula represents the end that, in operation of the unit 800, is inserted in the target tissue. FIG. 8B provides a different view of the unit 800. The internal hollow of the handle 804 is terminated, at the proximal end 804B, with an opening 808, while another end of the internal hollow of the handle 804 is operably connected to the hollow or lumen of the cannula at the distal end 1804A. In one embodiment, the handle 804 includes a thumb indentation 810 configured to ease of gripping and handling the unit 800.

During the harvesting procedure, for example, the harvesting cannula 802 is moved within the target tissue as vacuum pressure, which is transferred to the cannula 802 through the tubing 806 and the handle 804 and creates a force that, by a pressure differential, attracts a substance (such as adipose tissue) from the tissue to the region of lower pressure, via suction at openings (not shown) formed in a body of the cannula 800 (such as, for example, in a side wall of the cannula 800).

FIG. 8C illustrated a general view of a cannula and a blown-up cross-sectional view of a portion of it.

Figure 9A:
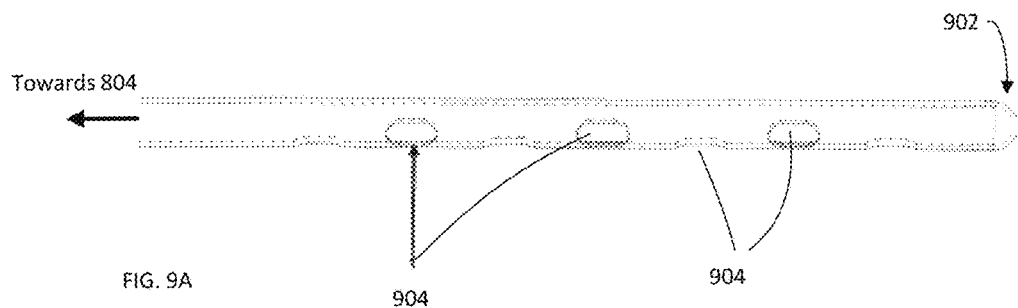
FIGS. 9A, 9B, 10A, 10B, and 10C provide additional details of cannula(e) structure(s).
Figure 9B:
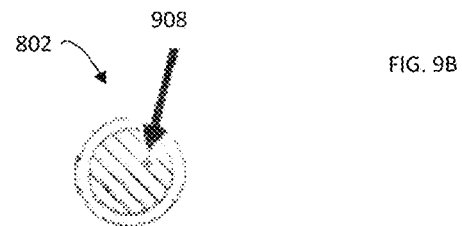

According to the idea of the invention, and in reference to FIG. 9A, a tip 902 at the distal end 802A of the cannula 802 is generally configured to be a rounded, machined end (referred to as herein as "blunt tip") that is closed off from suction (such as to terminate the longitudinal hollow of the cannula without axial access to the surrounding tissue) and has a smooth and even outer surface to cause no disturbance and/or destruction when brought in contact with the tissue. Here, the cannula 802 is shown with the openings or holes 904 in the side wall of the cannula. Notably, according to the idea of the invention, there are no harvesting or reinjection openings 904 present at the completely closed, blunt tip 902 and/or at the distal end 802A of the cannula 802, to avoid harvesting and/or reinjecting of fatty cells through the tip. Such configuration distinctly differentiates the cannula 802 from a needle, for example, which an open tip at the distal end 802A, often a sharp open tip. Often times, the side openings 904 are made to be oval in shape and under a square centimeter in area (but, generally, they are not limited to a specific shape and/or size). An embodiment of the cannula configured for harvesting generally includes more than one opening 904, while there is typically one or more openings 904 in the side wall of the cannula that is configured for reinjection of the adipose tissue. In a specific embodiment of the reinjection cannula, there is only one side wall opening 904. Among the multiplicity of cannulae of the kit of cannulae present invention, the dimensions of the openings 904 in different cannulae are substantially similar among the harvesting and reinjection cannulae. FIG. 9B illustrates a cross-section of the cannula with the longitudinal hollow (inner lumen) 908 in it.

Figure 10C:
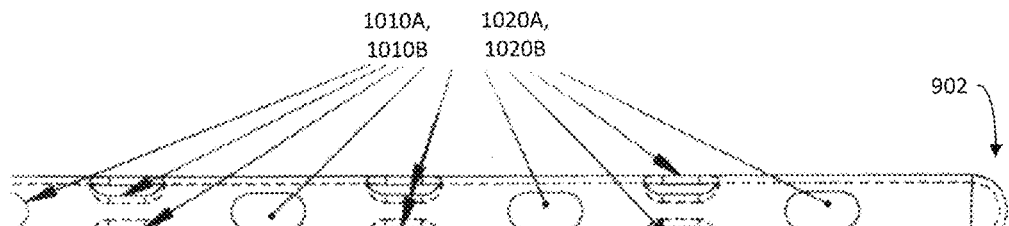
Figures 10A, 10B:
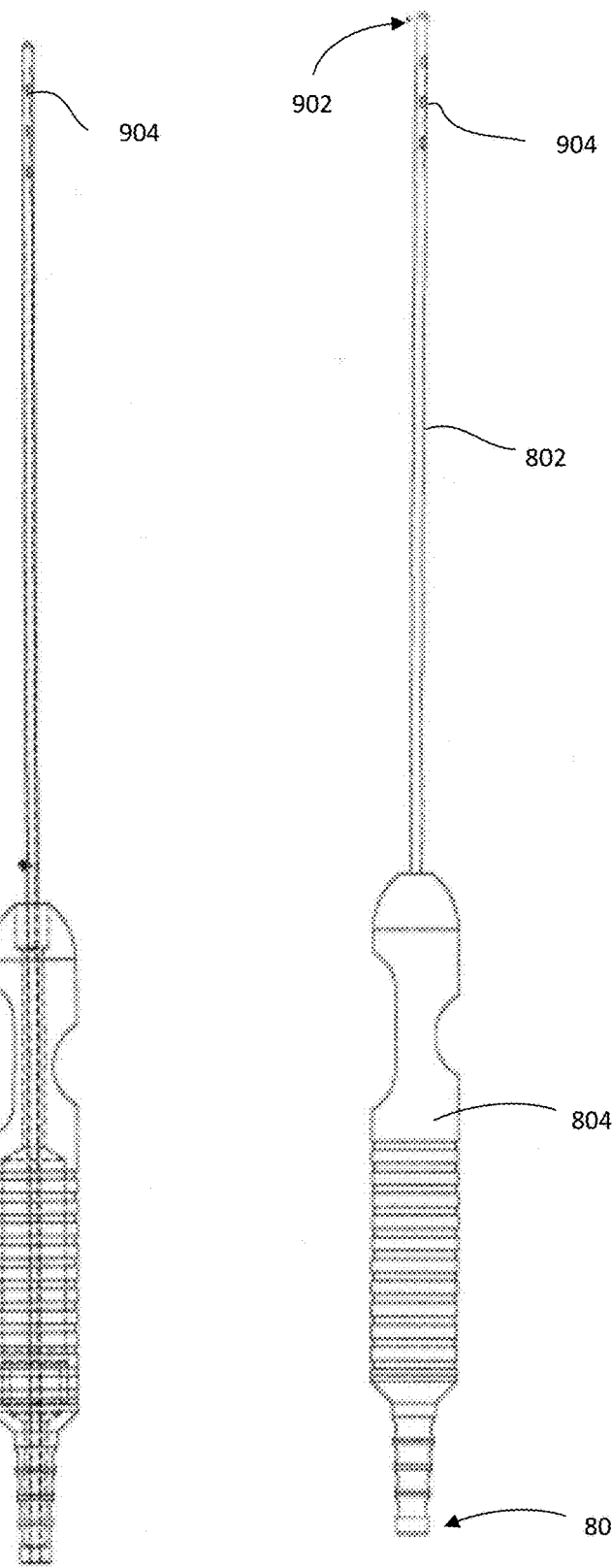

An example of the units 1000, containing cannulae configured according to an embodiment of the invention, is shown in FIGS. 10A, 10B (with internal passage or hollow or lumen fluidly connecting the openings 904 with the proximal end 804B of the handle 804 shown in the cannula of FIG. 10A in a dashed line).

It is appreciated that in an adipose tissue transfer system that includes the harvesting cannula and the (re)injection cannula, as well as the portions of the system connecting the one with the other, and that is configured to effectuate the real-time transfer of the just-harvested adipose tissue (to a location chosen for reinjection of such tissue), the openings in a side-wall and/or lumen of the harvesting cannula represent the most restrictive of all available fluid passages. Indeed, only those agglomerates of the adipose tissue are transferred down the stream of the transfer system towards the reinjection cannula that have passed through the inner lumen of the harvesting cannula. It has been empirically found that the appropriately size agglomerates are seamlessly transferred through the system and reinjected when the judiciously-chosen reinjection cannula is used.

Accordingly, one embodiment of the invention provides a kit or multiplicity or set of harvesting and reinjection cannulae (see FIGS. 10A, 10B). Harvesting and reinjection cannulae in such set are configured (for harvesting and/or reinjection of fatty cells during removal and/or reinjection procedures) with intentional and respectively-corresponding specifically-defined matching of structural and geometrical features to maximize viability of the harvested/reinjected (adipose) tissue and minimize procedure time.

The multiplicity of the side-wall openings in either of the harvesting or reinjection cannulae ensures that the adipose tissue transfer process continues regardless of whether a particular opening on either cannula is clogged or not, while the appropriate choice of the dimensions of openings of the harvesting cannula ensures that the agglomerates of the adipose tissue not fitted to pass through the inner lumen of the harvesting cannula are not harvested to begin with. This "multiplication" of the openings is schematically illustrated in FIG. 10C, where the operational redundancy is provided by the duplication of the openings on opposite sides of a wall of the cannula (see openings, 1010A, 1010B; 1020A, 1020B), for example.

The Front and End Portions of the Transfer System.

Referring again to FIG. 1A, adipose tissue includes many small adipocytes held together by fibers in larger agglomerates. During the liposuction procedure, the aspiration or harvesting cannula 102 removes these agglomerates, together with other cells and fluids, including saline solution, blood and oil. The aspiration (or harvesting) cannula 102 includes a long, hollow (typically metal) tube with one or more openings near the distal end, as discussed above, and extending through a hand piece or handle 122. In operation, the aspiration cannula 102 is inserted into a first region of a target bodily tissue 116 (in case the target tissue is the subject's body, such insertion can be carried through a small incision in the skin). With the source of vacuum 104, attached to the aspiration cannula 102, the adipose tissue is pulled from the harvesting site 116 through the openings on the side-wall (not shown in FIG. 1A) of the aspiration cannula 102.

The fat harvesting container 106 is fluidly connected to both the outlet 126 of the combination of the aspiration cannula and the handle, and the source of vacuum 104 by a section of flexible tubing 118, such that the adipose tissue sucked out from the first region of the target tissue 116 is deposited and/or stored in the harvesting container 106. The container 106 may include a suitable biocompatible and sterile storage volume or collection container configured to accept and/or store the bodily fluid. Similarly, the flexible tubing 118 may comprise any suitable hollow delivery channel with first and second ends, where the ends can be fluidly connected (i.e., connected in a fluid-tight configuration) with the storage volume (e.g., the fat harvesting container 106) and the aspiration cannula 102.

During the aspiration (harvesting) step of the adipose tissue transfer procedure, vacuum in the range from about 10 inHg to a negative one atmosphere of pressure (of vacuum of 29.9 inHg) is typically used, with 18 inHg of negative pressure mentioned in some related art publications to be a recommended maximum level of vacuum to assure cell viability. A skilled artisan will readily recognize that the negative pressure applied to the adipose tissue being aspirated may preferably be set at such workable levels that are necessary to achieve fat removal from the specific harvested site—and no more. These levels, however, should not be "set in stone" and/or defined a priori (such as provided by the system discussed in U.S. Pat. No. 8,968,272, for example), as such levels vary from patient to patient and are often different from the arbitrarily chosen level (be it 18 inHg or a particular different fraction of one atmosphere). The levels of pressure applied to AT during the reinjection portions of the procedure should not be defined a priori for the same reason, but rather identified based on effect(s) produced by the reinjection procedure on the recipient body.

Moreover, it has been empirically found that even while levels of negative pressure required to harvest adipose tissue—as well as levels of positive pressure appropriate for reinjection of the AT—vary from patient to patient, such levels also vary from location to location in the target tissue (for example, in the body of the same patient). This finding unequivocally indicates to the skilled artisan that a clinician, performing the adipose tissue transfer, generally cannot rely on the unsubstantiated prescriptions of which level of vacuum (or positive pressure, in case of re-injection) is or is not appropriate for the procedure and should select such level(s) from a wide range of pressures that would be required to achieve optimal results. What is important to ensure the adipose tissue viability, however, is that the modulus of the value of pressure imposed onto the already harvested tissue does not exceed the pressure level at which such tissue was harvested to begin with. The system of the invention is judiciously dimensioned to ensure such result. At the same time, an embodiment of the invention is devoid of any additional fluid channels joining (merging, incorporated with) the reinjection portion of the AT delivery channel between the contained 106 and the output end of the cannula 110 with the purpose of pressuring the AT between these two points (contrary to what the system of US 2006/0224144 employed), thus ensuring that there is only one, single delivery channels in a reinjection portion of the system.

During the aspiration step of the procedure, a scale 112 and a vibrating table 114 can also be used. By placing the tissue harvesting container 106 on the scale 112, the amount of adipose tissue removed from the first region of a subject's body 116 can easily be tracked. Due to the nature of the adipose tissue, it naturally separates from the other material that is aspirated (e.g., debris, oil, blood, infranate) and is more or less separated, spatially from other material contents of the harvesting container 106. Vibrating or shaking the fat harvesting container 106 with, for example, a vibrating table 114, can be used to speed the process of separating the adipose tissue from debris, oil, blood, infranate, and saline.

Figure 2:
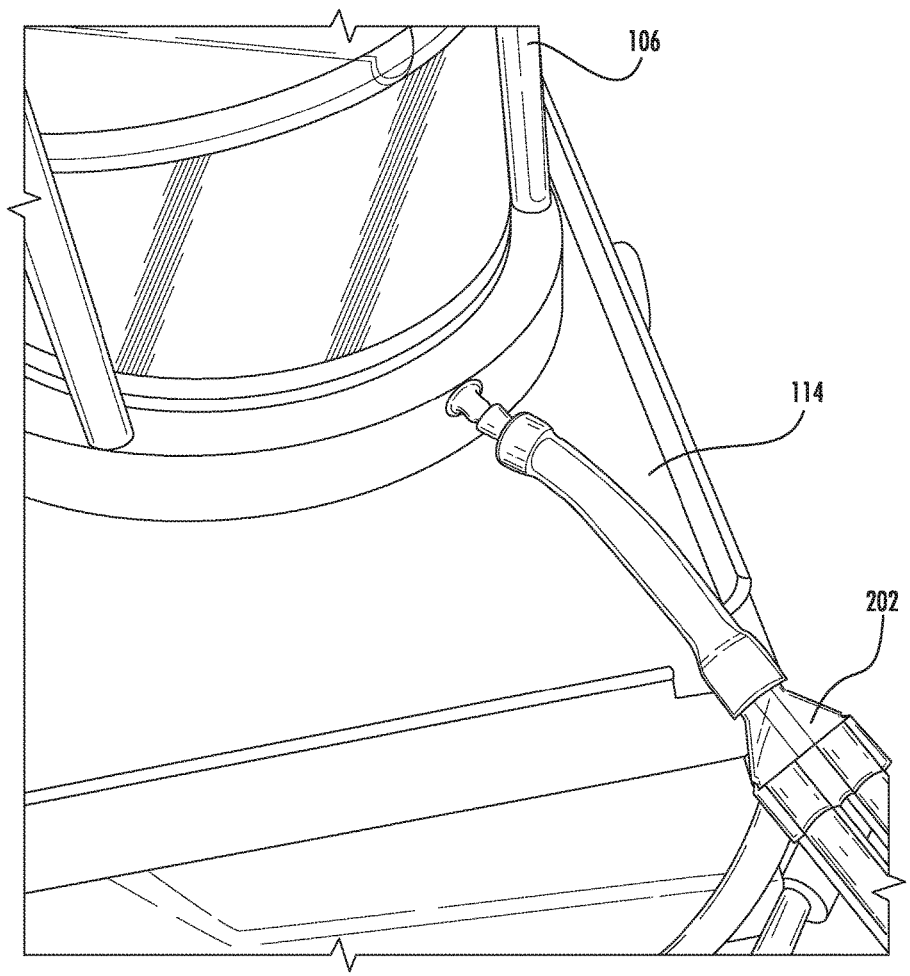
FIG. 2 is a perspective view of an embodiment of a fat harvesting container with a connected dual output port.

Once the adipose tissue is separated, the auxiliary fluids (blood, and infranate) can be bled off from the bottom of the harvesting container 106, through the use of a connected dual output port 202, shown in FIG. 2. While one of the outputs of the dual output port 202 is used to drain away the undesired (auxiliary) aspirated material, the other of the outputs is connected to flexible tubing 118, which is run through the reinjection pump 108 and is eventually connected to the reinjection cannula 110. The fluid connection provided by the flexible tubing 118 through a hollow delivery channel thereof is used for the step of reinjection of the adipose tissue from the container 106 through the reinjection cannula 110 to the target reinjection site 120. In particular, after completing the draining of the undesired aspirated material from the container 106 though one output of the port 202, a corresponding valve of the port 202 can be closed to allow the flow of the target adipose tissue from the harvesting container 106 to a second region (target site) 120 of the subject's body, or injection site 120, via the flexible tubing 118 and reinjection cannula 110.

Embodiments of the cannulae kit (aspiration and reinjection cannulae) for use with the transfer system are discussed above. The inventors are unaware of related art evidencing that the above-identified dimensional features of the cannulae for use with the AT transfer system described in this application (employed one at a time or in combination with one another) not only improve the efficiency of reinjection of AT that has (or is being) harvested at any appropriate vacuum pressure up to negative 1 atmosphere, but also ensure the uninterrupted transfer process free of clogging, while, at the same, allowing the system to control the internal pressure in the delivery channel in real time and modify the transfer process once the pre-determined level of pressure has been crossed. In that, the implementation of such dimensional features was shown to achieve a result unexpected by related art.

In the case of a clog of the system, even greater—usually excessive—positive pressure is applied by the systems of related art to clear the clog. A clog occurs when oversized agglomerates occlude the pathway for adipose tissue. Clogs can be hard to locate, and both time consuming and labor intensive to clear, so current solutions includes increasing the internal pressure in the adipose-tissue transfer channel to force the occlusion to clear. Such positive pressures can reach 40 psi (about 80 inHg) or more in syringe-based systems, which is understandably may be substantially higher than the pressure levels used during the aspiration step of the overall procedure. When excessive pressures do not alleviate the clog in the system, a metal rod (referred to as a stylet) is often inserted into the inner lumen to dislodge the clog, which can cause damage to the adipose tissue.

The related art mentions the control of the flow rates and pressures during the aspiration (harvesting) step. However, during the aspiration of the tissue from the site 116 the vacuum level cannot be reduced below negative 1 atmosphere level, so regardless of how fast the flow rate is from the site 116 to the container 106, this pressure level is not exceeded. Contrary to this limitation of the aspiration step, during the reinjection step the pumping action is employed to move the adipose tissue from the container 106 to the site 120, and significant pressures can be reached in practice. The related art does not seem to provide any indication that a specific difference between the pressure levels during the aspiration and reinjection steps of the procedure may and, in fact does, present complications for keeping the reinjection site (that is, the recipient of the harvested AT) safe. The continued procedural uncertainty, in related art, about the details of the reinjection procedure begs a question: at what levels of reinjection pressure, created at the recipient site, should the AT transfer system's operation be halted or reversed?

Therefore, judicious real-time control and adjustment of at least pressures during the process of reinjecting (and, generally, handling of) adipose tissue remains an unaddressed need. The reinjection pump 108, utilized in the system 100 according to the idea of the current invention, is configured to maximize the flow rate of the adipose tissue, while at the same time controlling and adjusting the positive pressure levels in the tubing 118, the reinjection cannula 110, and the injection site 120 in real-time.

A person of skill in the art will readily appreciate that, during the AT reinjection procedure, the recipient site is subject to at least two types of trauma: one is concerned with the back-and-forth repositioning of the reinjection cannula at the recipient site (typically employed by a surgeon in attempt to more evenly distribute the AT across the reinjection site), and another—the pressure build-up created by the reinjected AT that may and often does—at some levels compromise the reinjection site blood vessels by weakening the vessel walls (forming an aneurism of sorts) and causing the penetration of fat into blood vessels and, in this case, fat embolism. The question of vessel rupture subject to external pressure has not been investigated by related art. At the same time, empirical results related to critical pressure for arterial wall rupture in human cerebral arteries provided indication that, being age dependent, the average rupture (arterial wall compromise) pressure is about 2.21+/−0.59 atmospheres (with the range from about 1.13 to about 4.3 atmospheres), while at the same time not showing any significant dependencies on the vessel origin, vascular configuration, direction of the rupture, or the presence of coexisting pathologies. According to the idea of the invention, an embodiment of the invention provides a tool for measurement and recordation of AT reinjection pressures at the reinjection site and resulting effects of such pressure, while being configured to alter the reinjection procedure once the pressure at the reinjection site reaches a level at which an arterial wall is compromised (with such pressure being measured directly or with respect to the pressure at the aspiration site).

In further reference to FIG. 1A, the reinjection side of the system 100 includes the a fluidly uninterrupted channel for delivery of the harvested adipose tissue all the way to the injection side 120, and includes a flexible tubing 118 that remains structurally uninterrupted from its first end (in operation attached to the contained 106) to its second end 128 (in operation attached to the distal/input end of the internal lumen of the handle 130 of the reinjection cannula 110). Such choice of a continuous piece of tubing throughout the reinjection portion of the system 100 eliminates any structural transitions and/or changes in the lumen diameter at least until the adipose tissue is transferred all the way to the handle 130/cannula 110, thereby facilitating the maintenance of the viability of the live adipose tissue. In one case, each of the handles 122, 130 includes an inner lumen the diameter of which varies along the lumen.

Figure 3:
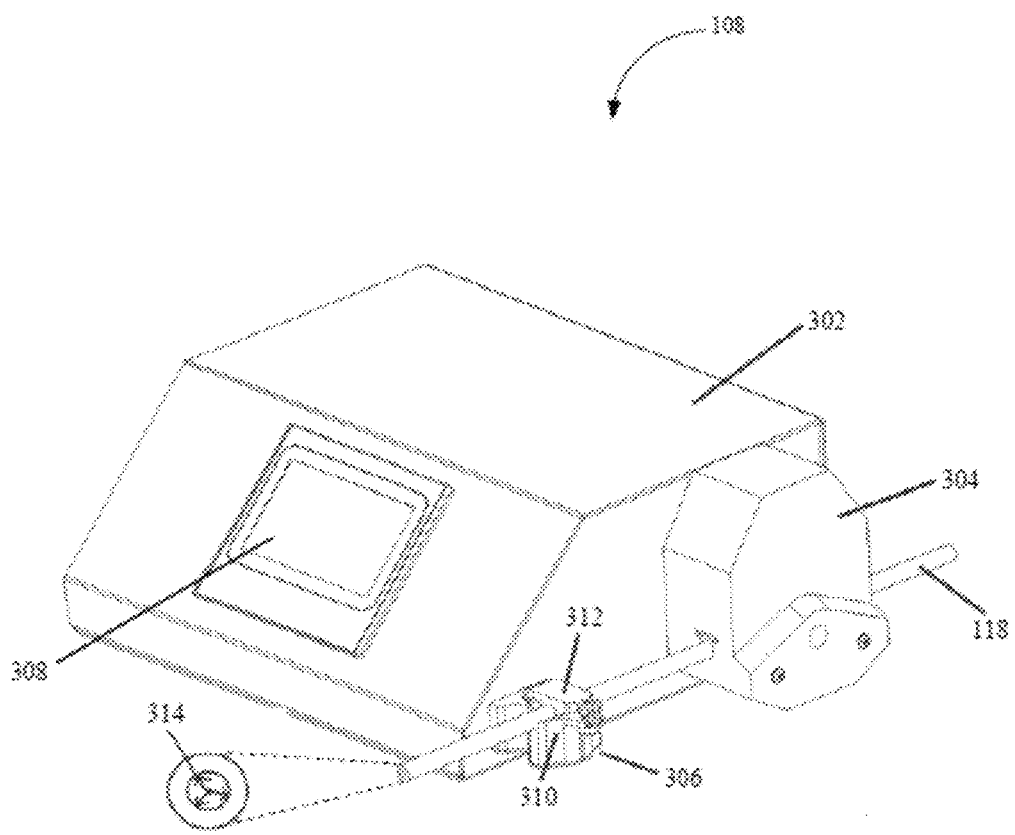
FIG. 3 is a perspective view of the reinjection pump with a blown-up cross-sectional view of a hollow delivery channel.

Referring now to FIG. 3, the reinjection pump 108 includes a protective housing 302, a peristaltic pump head 304, and an external pressure sensor 306. The housing 302 may be formed from metal, or of any other suitable rigid material, for example, a molded plastic or polymer. The housing 302 is dimensioned to enclose all of the electrical and control components of the reinjection pump 108, the operation of which may be controlled or governed via a touchscreen 308.

The reinjection pump 108 employed in the embodiment includes a (programmable processor/data-processing unit/PC) as part of the system (not shown for simplicity of illustration), with the purpose of providing various control functions. The touch screen 308 allows a user to set variables and settings of the operation of the reinjection pump 108. For example, possible settings may include the revolutions per minute of a DC motor of the pump 108, a desired limit of the pressure created in the reinjection channel between the pump 108 and the site 120, or a number of pulses per minute for the pulse-mode of reinjecting the adipose tissue. Each of these settings is described in greater detail below.

The peristaltic pump head 304 is connected to or even mounted to a DC motor contained in the housing 302. The DC motor is configured to rotate in both forwards (for example, clockwise) and backward (for example, counterclockwise) directions. The external pressure sensor 306 comprises a base 310 and a hinged top 312. The external pressure sensor 306 is configured to monitor the internal pressure in the inner lumen 314 of the flexible tubing 118, as shown in the blown-up portion of FIG. 3. The value of measured internal pressure in the inner lumen 314 is transmitted to the control component(s) of the reinjection pump 108, for example, in a form of an electrical signal. The external pressure sensor 306 may be connected to the housing 302 or may be a free-standing device that provides the reinjection pump 108 with the necessary feedback of internal pressure.

Figure 4:
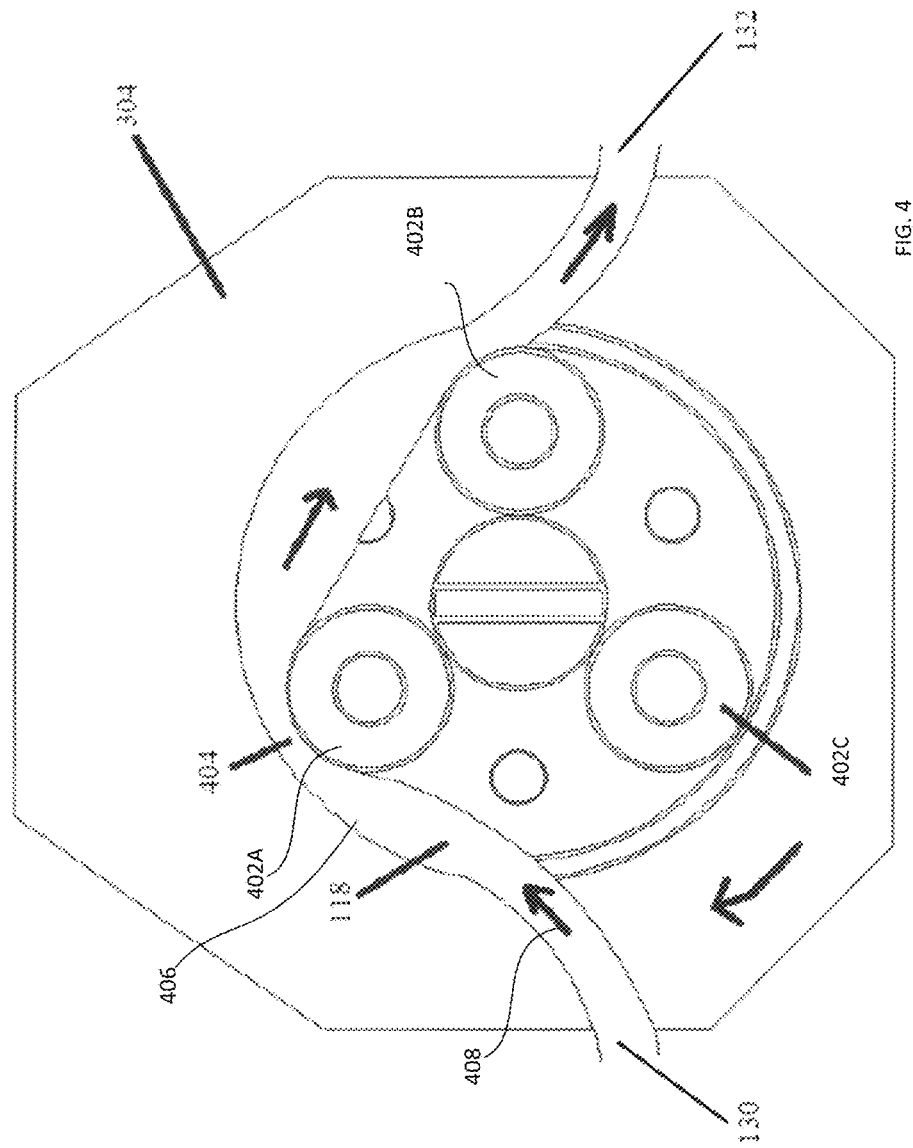
FIG. 4 is a cross-sectional schematic of a peristaltic pump head.

FIG. 4 shows a cross-sectional view of the peristaltic pump head 304 with the flexible tubing 118 installed. The peristaltic pump uses positive displacement to move material through the pump, where the positive displacement is created using multiple rollers 402A, 402B, 402C. As the DC motor turns the rollers 402A, 402B, 402C, one of the rollers 402 (as shown—402A) pushes the tubing 118, passing through the pump, against the surface of the pump head 304, thereby creating an area of a slightly elevated internal pressure causing slowing of the flow and/or temporary occlusion by compressing a portion of the tubing 118 (see region 404). As one of the rollers 402A, 402B, 402C moves past the compressed area 404, the flexible tubing 118 tends to resume its normal shape (see region 406). This creates and defines a reduced or even negative pressure (suction) side 130 of the reinjection pump 108 with respect to the portion of the tubing 118 that is located in the area 406, thereby drawing in more fluid, as shown by the arrow 408. The fluid trapped before the compression point 404 is forced forward and creates a positive pressure side 132 of the pump 108. Before the first roller releases the compression area 404, the roller behind it initiates a new compression area 404, and the process is repeated. Thus, the rollers 402A, 402B, 402C are configured to act as both the pumping mechanism and a "pump valve" to separate the positive and negative pressure sides or regions of the reinjection pump 108. Accordingly, in an embodiment of the invention the reinjection pump is devoid of an actual component configured to operate as a dedicated valve (that is as a device that movably opens, shifts, or partially obstructs a flow of the fluid through the tubing by blocking a passageway of the flexible tubing internally to the tubing): instead, the function of a pump valve is performed by the fluid-pumping elements of the pump, such as rollers.

Figure 5:
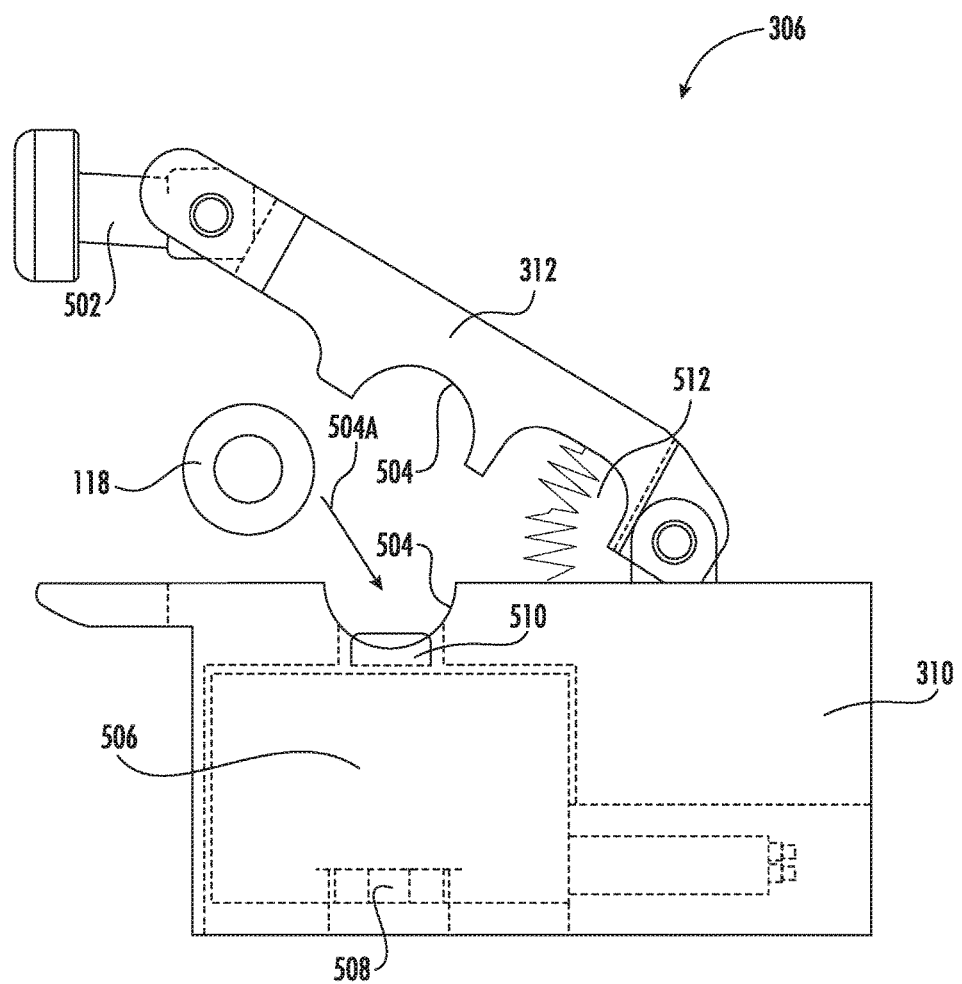
FIG. 5 is a schematic diagram showing, in side view, an embodiment of the pressure sensing device in an open configuration.

FIG. 5 shows schematically a side view of an embodiment of the external pressure sensor 306 in an open configuration. When the locking mechanism 502 is released, the hinged top 312 opens to allow the flexible tubing 118 to be installed into the tubing channel 504, as indicated by an arrow 504A. Both the base 310 and the hinged top 312 each have half of the tubing channel 504, the dimensions of which are chosen to substantially match the outer diameter of the flexible tubing 118 when the external pressure sensor 306 is in a closed configuration. A transducer/load cell 506 is rigidly attached to the base 310 at a connection point 508. A sensing component 510 of the transducer/load cell 506 is dimensioned to protrude into the tubing channel 504. When the flexible tubing 118 is placed into the tubing channel 504, the hinged top 312 is closed, and the locking mechanism 502 is engaged to prevent the hinged top 312 from moving and to create a rigid support for the flexible tubing 118 to press against. A spring mechanism 512 may be used to hold open the hinged top 312 when the locking mechanism 502 is not engaged. The spring mechanism 512 also provides a force to keep the locking mechanism 502 engaged when the external pressure sensor 306 is in the closed configuration without any flexible tubing 118 in the channel 504.

Figure 6:
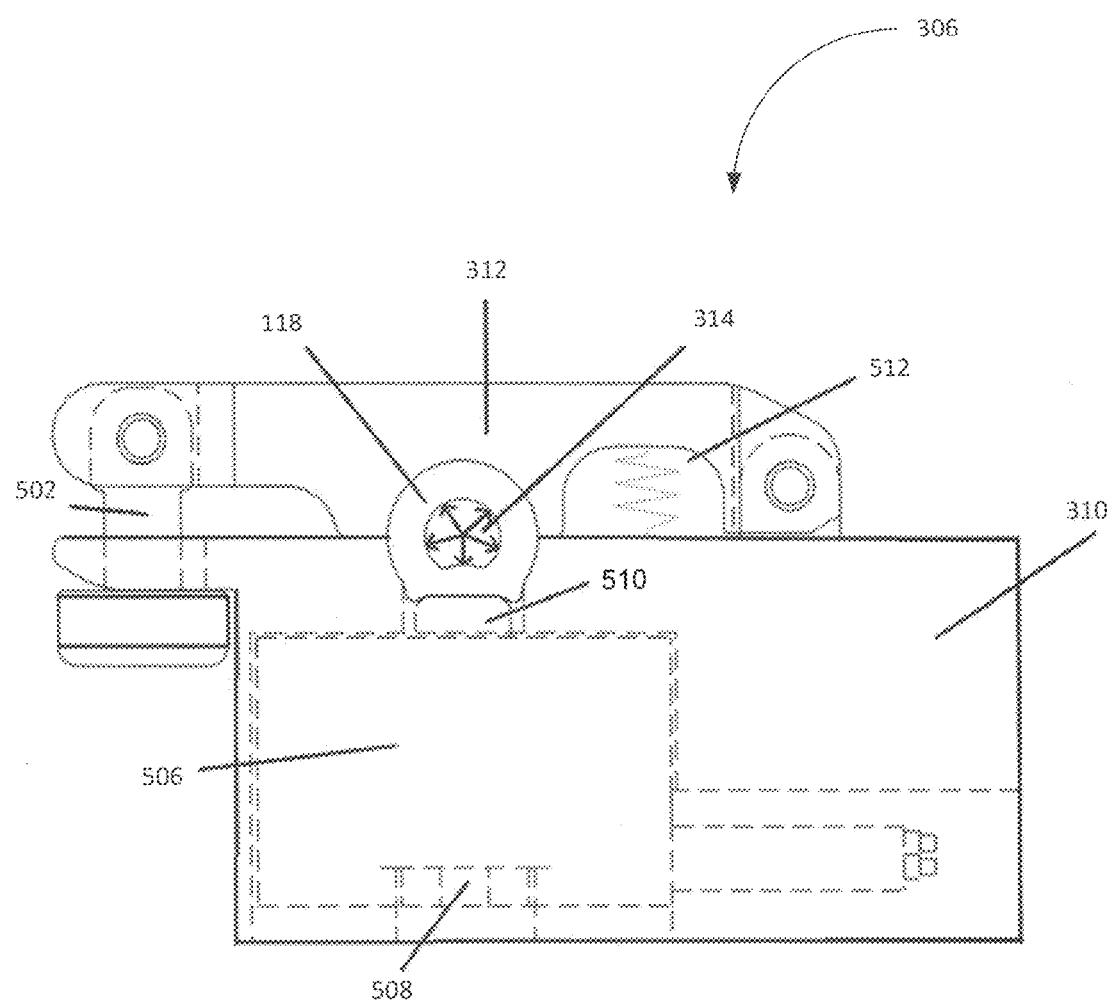
FIG. 6 is a side view of a pressure sensing device in a closed configuration, according to an embodiment of the invention.

FIG. 6 illustrates, inside view, an embodiment of the external pressure sensor 306 in a closed configuration with the flexible tubing 118 installed. FIG. 6 represents the deformation of the flexible tubing 118 when it is pressed against the sensing component 510. With the transducer/load cell 506 rigidly attached to the base 310 at connection point 508, the only part of the shown contraption that can move is the sensing component 510, and such movement of the component 510 is further transferred to deform the internal structure of the transducer/load cell 506, which contains a strain gauge. The flexible tubing 118 is confined by the tubing channel 504 and does not substantially expand in any direction except towards the sensing component 510. This ensures that the geometric/volumetric expansion of the flexible tubing 118 (for example, a change in a geometrical parameter of the tubing such as the diameter of the tubing), caused by the force that originated due to the internal pressure of the inner lumen 314, is directed towards the sensing component 510. This force, which is defined as a force over a specific area, varies proportionately with the variation of the internal pressure of the inner lumen 314 of the flexible tubing 118. Accordingly, an accurate and/or precise output (for example, in the form of the electrical signal produced by the transducer/load cell 506 and/or programmable processor of the system) that represents the internal pressure of the inner lumen 314 can be derived. In one embodiment, therefore, the pressure sensor includes a transducer configured to measure an internal pressure of the adipose tissue in the hollow delivery channel of the system by measuring a change in a parameter (of the hollow delivery channel) caused by such internal pressure.

The operational advantage provided by the above-described sensor is that it is external with respect to the channel 118, and thus does not require any direct contact with the contents of the transferred fluid (the adipose tissue) located inside the flexible tubing 118. This facilitates maintaining sterility and the entire external pressure sensor 306 is reusable. Reusability increases the accuracy and ease of use by eliminating installment/reinstallment steps as well as repeated calibration steps, which are conventionally taken in operation of the system(s) of related art.

In further reference to FIGS. 1, 3, 5A, 5B, 8A, 8B, 8C, and 10A, 10B, for example, the inner diameter(s) of the lumen(s) of the reinjection cannula 110 and a corresponding handle 130 is/are typically much smaller than the diameter of the inner lumen 314 of the flexible tubing 118. The inlet 810 of the reinjection cannula unit features a machined taper 604 configured to help to guide and funnel the agglomerates of adipose tissue into the (optionally smaller) inner diameter of the reinjection cannula 110, thus preventing the adipose tissue from clogging and/or shearing at the transition point between the flexible tubing 118 and the reinjection cannula 110.

The embodiment, as described, is configured to maintain a smooth, spatially continuous lumen or channel throughout the entire transfer system 100. After the adipose tissue leaves the harvesting container 106, the reinjection portion of the system transfers the adipose tissue along the flexible tubing 118 until it reaches the reinjection cannula 110. By configuring the system to avoid and/or to remove choke points and small orifices to squeeze through (such as luer lock fittings and one way valves, conventionally used in the systems of related art), the adipose tissue is aided in gently flowing along the path defined by the flexible tubing 118. The pump used to cause the adipose tissue to move through the flexible tubing 118, only contacts an outer surface of the flexible tubing 118, thus eliminating the need to sterilize a component of the pump. The system contains only one, single, unique biocompatible component that has an active role in contacting the adipose tissue while it is transferred from the harvesting container 106 to the reinjection cannula 110, and this is the flexible tubing 118. This flexible tubing 118 comes in disposable, pre-sterilized packs to allow a sterile environment for the adipose tissue.

Controlling Parameters of the Transfer Process.

The controllable settings of the reinjection pump 108 allow a user to maximize the flow rate of the adipose tissue, while at the same time controlling the positive pressure levels in the tubing 118, the reinjection cannula 110, and the injection site 120.

The setting for revolutions per minute (RPMs) is referred hereafter as the speed of the motor and relates to the revolutions per minute of the rollers (shown as 402A, 402B, 402C in FIG. 4) of the peristaltic pump head 304. Controlling the speed of transfer of the adipose tissue from the harvesting site to the reinjection site is very important feature of the procedure that is not paid attention to by related art. The reason for actively controlling this speed is caused by the fact that there is an actual limit on the flow of the adipose tissue through the flexible tubing 118 and the reinjection cannula 110. The main flow restriction is provided by the diameter of the inner lumen of the reinjection cannula 110. An embodiment of the present invention is configured such that, when the speed of fluid transfer is set too high, the adipose tissue is pushed into the flexible tubing 118 faster than it is allowed to leave the tubing 118, which immediately increases the internal pressure and triggers the upper pressure limit control of the reinjection pump 108.

The pressure limit expressly set by the user for the reinjection pump is preferably the maximum internal pressure desired inside the flexible tubing 118. If the external pressure sensor 306 detects a pressure that exceeds this pressure limit, the programmable processor is programmed to stop the motor and to reverse the pumping direction until the internal pressure is reduced to near zero. The zero pressure value is defined as the internal pressure that exists in the flexible tubing 118 when the pressure sensor 306 is zeroed before the harvesting/reinjection procedure is started. In one embodiment, the user must release and press a switch to resume normal forward pumping. The observation of the pressure limit with the use of the external pressure sensor 306 automatically limits the pressure in the tubing 118, and allows the clinician to focus on more important matters, such as placement of reinjected tissue.

Another operational feature that is controlled by the programmable processor of the system includes configuring the mode of reinjection of the adipose tissue into the target reinjection site 120.

On the one hand, configured as described above, the system is structured to react to the pressure formed by the being-reinjected adipose tissue at the recipient (reinjection) site. Indeed, due to the limited compressibility of the adipose tissue, when and if the pressure at the distal end of the adipose-tissue-transfer channel (for example, in the vicinity of the side-wall opening of the reinjection cannula) exceeds the specified threshold established for the reinjection site, the pressure sensor kicks in and causes the system to modify the reinjection procedure. As was already alluded to above, different reinjection sites (that is, different portions of the recipient body) may and do required different pressure limits to ensure the reinjection site safety. The tolerance of the reinjection site to the pressure caused on the site by the being-reinjected adipose tissue is clearly very different for an extremely sensitive facial areas (such as those around the eyes, for example) and the buttocks tissue, and piercing of the former is likely to occur at a much lower pressure level than that of the latter.

Figure 11:
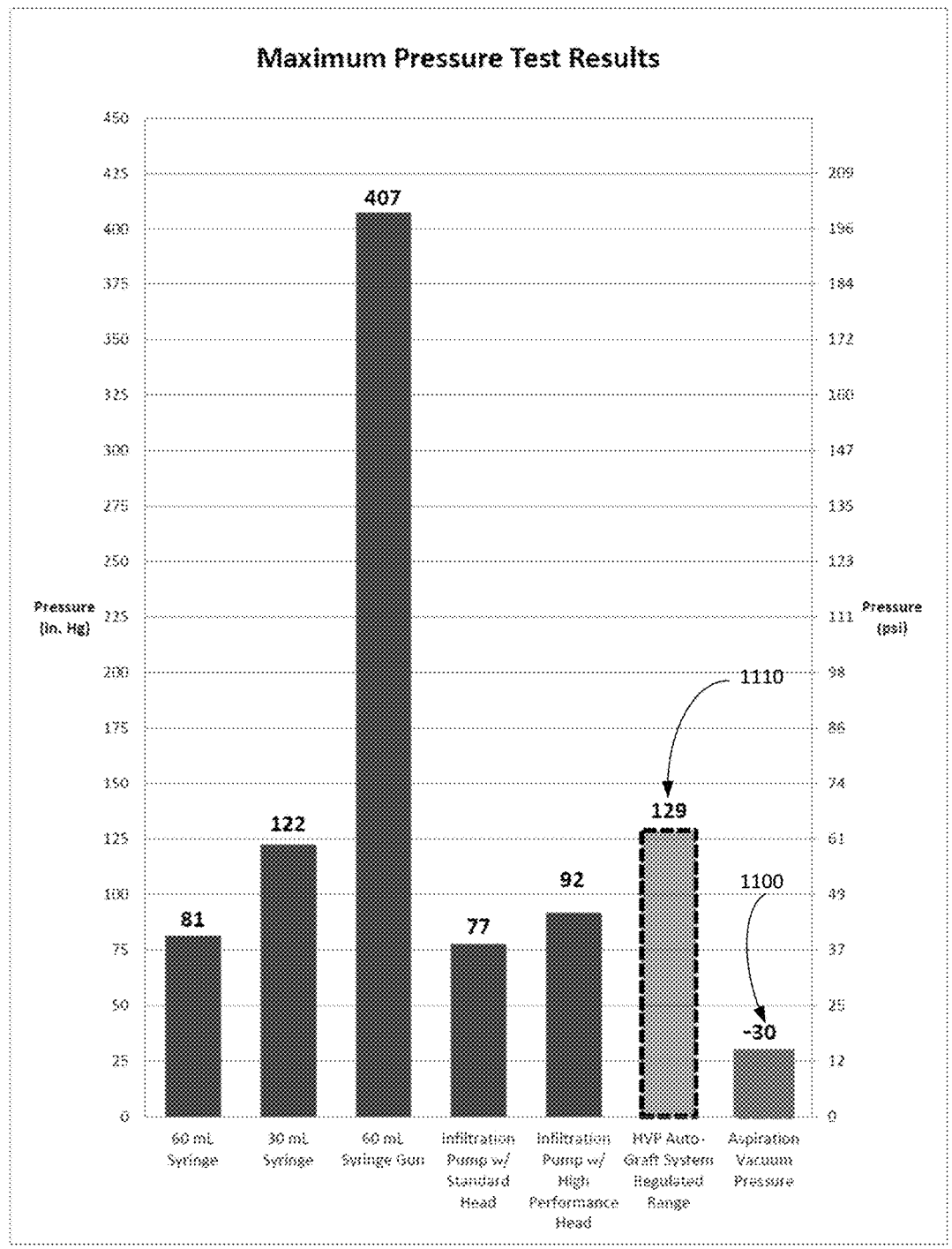
FIG. 11 illustrates the results of testing positive pressure caused by some of commonly-used adipose-tissue reinjecting devices.

To this end, the plots of FIG. 11 show—for different groups of devices commonly used for fat transfer—the levels of positive pressure produced by such devices at the output under the "clogged" conditions. (The test setup utilized to empirically procure these dependencies included a liquid-filled pressure gauge attached to a metal luer thread using a piece of flexible tubing, in absence of air-bubbles.) Syringes were tested by operating them with one hand. A person of skill in the art will readily recognize that, in absence of the intentional real-time pressure adjustment mechanism, and while the modulus of one considered reinjection pressure preferably should not exceed the level of about 29.9 inHg or about 1 atmosphere (equal to that of a pressure level on aspiration that may be preferred to aspire the viable AT tissue, referred to and defined herein as a "practical aspiration pressure", shown for comparison as 1100), if maintaining the viability of the AT cells during the AT transfer is a priority, practically every reinjection methodology produced positive pressures substantially exceeding this tentative level. (Just as an example, the fat embolism is most certain to occur when carrying out the reinjection procedure in the facial region with a syringe. While a syringe-based system disclosed in U.S. Pat. Nos. 8,968,272 and/or 8,360,102 establishes some—fixed, intentionally maintained at a constant level—control of pressure associated with the handling of the adipose tissue, the discussed mechanism lacks not only the ability of ceasing the movement of the adipose tissue through the mechanism if and when required, but also the ability to adjust, in real-time, a degree/level of control of pressure and ability to set the desired control threshold depending on the type of recipient (aspiration) and/or harvesting site. (For example, the threshold value of pressure acceptable for a recipient site at a face of the patient differs from that for a recipient site at a limb, and differs from that for a recipient site in the abdominal area, and further may differ from that for a recipient site in a buttocks area.) In other words, a person of skill will readily recognize that the system of U.S. Pat. Nos. 8,968,272 and/or 8,360,102 is incapable of and simply should not be used for adipose tissue handling with different recipient sites.

A skilled artisan would also immediately recognize that, in addition or alternatively, such system—as well as any other system and/or methodology of related art—is configured to ensure any of (i) the controlled AT transfer operation, which can be interrupted or reversed at any chosen pressure level within the range of pressures that does not exceed the practical aspiration pressure level, modulus wise, at the recipient site and/or in a hollow of the channel of the AT transfer system, and/or (ii) the controlled AT transfer operation, which can be interrupted or reversed at any chosen recipient-site (and/or in a hollow of the channel of the AT transfer system) pressure not exceeding a level causing rupture of a blood-vessel wall(s), and/or (iii) the controlled AT transfer operation, which can be interrupted or reversed at any recipient site (and/or in a hollow of the channel of the AT transfer system) pressure level not exceeding the modulus of the practical aspiration pressure level by as little as about 0.13 atmosphere and as much as about 3.3 atmosphere (and, preferably, by as little as about 1.21 atmosphere and as much as about 1.8 atmosphere). Notably, in contradistinction with related art, embodiments of the present invention are configured to satisfy any of the above conditions (i), (ii), and (iii) during operation.

For the same reason, such system is not configured to allow for increase of pressure applied inline to the adipose tissue (internally to the tubing along which the adipose tissue is being transferred) within the pre-determined safety limits to clear temporary clogging. Similarly, the well-established methodologies of using the syringe-based systems for aspiration such as that described, for example, in U.S. Pat. No. 5,052,999, simply are not configured to regulate the vacuum pressure levels. An alternative version of such system, utilizing a peristaltic pump, only possesses settings for flow rate and ignores positive pressure levels entirely. At the same time—and in stark contradistinction with the lacking-real-time-control-of pressure methodologies of the related art, a reliable pressure of adipose tissue and its control (at the reinjection site) at any and every level of pressure not substantially exceeding the blood-vessel-wall's rupture pressure is established with an HVP Auto-Graft System of the present invention, as indicated in FIG. 11 with a numeral 1110 denoting the range of (substantially uninterruptingly variable) level of control of pressure, in the hollow of the AT transfer system of the invention. In a specific case, such system may be configured to avoid the situation when the system operates while a substantially constant pressure is applied over the full excursion of its plunger.

Figure 12B:
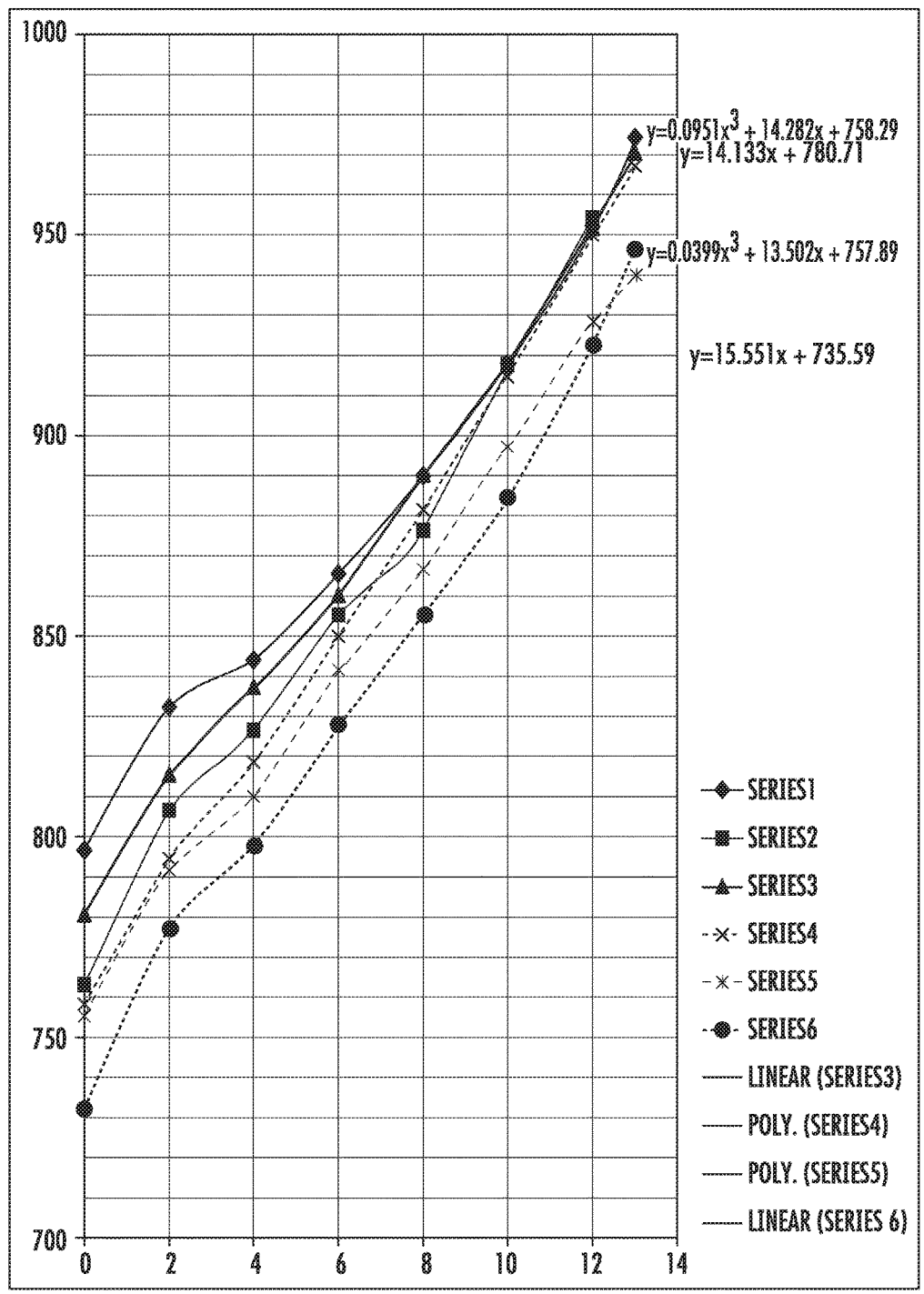

It may be beneficial to establish an empirical guideline based on which pressure limits should be established, as a function of a nature of a recipient site or of another parameter of interest during the reinjection procedure. To achieve this goal, it may be preferred to carry out the calibration procedure while measuring the pressure caused by the flow of the adipose tissue at end of the transfer channel that is close to the recipient tissue (as a non-limiting example, in the vicinity of the side-wall opening of the reinjection cannula). FIGS. 12A, 12B illustrate an example of one calibration procedure, with the horizontal axis of the plot of FIG. 12B representing pressure levels (psi) applied to the fluid-carrying tubing of the reinjection portion of the transfer system and the vertical axis of the same plot showing the output signal produced by the load-cell sensor of the embodiment (in absence of direct contact with the fluid contents of the tubing), in mV. Based on this type of the raw data, the safe pressure limits can be reasonably established.

On the other hand, in advantageous addition to a generally allowed continuous-flow mode of deposition of the adipose tissue to the reinjection site, in a specific case the system of the invention is configured to not only operate in a pulsed mode (that is, in a fashion when the continuity of the flow towards the reinjection site is interrupted according to a predetermined schedule) but also to allow, in such pulsed operation, to set a pulse frequency—for example, a number of pulses per minute—and/or a pulse duty cycle to form a desired pattern of the flow of the reinjected adipose tissue to the reinjection site 120. The desirability of such operation is suggested by the empirical results that indicated a more efficient blood-flow supply that the biological tissue at the reinjection site establishes to the so-deposited fat globules. The pulsed mode of reinjection is shaped and controlled with the programmable processor by maintaining the forward rotation of the peristaltic pump head 304 for a short period of time, followed by stopping the pump, and then repeating these two steps. When set correctly, the pulses propagate through the fluid in the flexible tubing 118, with the effect that the fluid exits the proximal (to the site 120) end of the reinjection cannula 110 in small boluses, or droplets, in a fashion that is maintained throughout the duration of the pulsed reinjection process. Setting the system 100 to operate in such a mode facilitates, but does not require, the elimination of the back-and-forth motion of the clinician's hand (with the use of which during a conventionally-carried-out reinjection procedure the desired reinjection results are achieved) by automatically placing a segmented array of boluses during a straight, non-reciprocal movement of the tip of the reinjection cannula 110. Controlling the bolus size is an important factor in maintaining adipose tissue viability by spacing out the agglomerates and maximizing vascularization. Accordingly to an embodiment of the invention, therefore, a method for reinjection of the adipose tissue is devoid of a reciprocating movement of the tip of the reinjection cannula.

Figure 7:
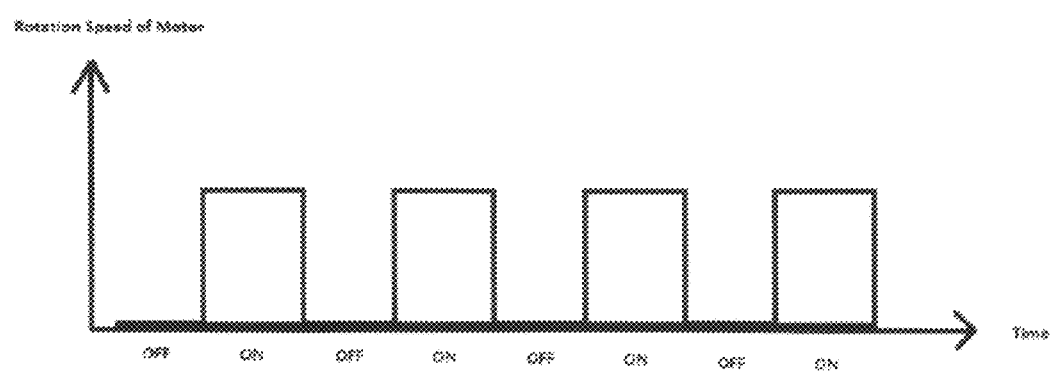
FIG. 7 is a graphical representation of the pulsed-mode reinjection function of the reinjection pump, according to an embodiment of the invention.

FIG. 7 is a plot illustrating the adipose-tissue flow distribution pattern and how it is controlled in real-time during the pulsed mode of operation of the system. The pulsed mode of operation can be set using two variables (the rate of the "stop-and-go" motion, and the speed of the motor during each portion of the "go" motion). The purpose of operating the system 100 in the pulsed mode is to create separate, segmented boluses of adipose tissue that exit the reinjection cannula 110 towards the reinjection site 120. The rate of the stop-and-go motion can be represented with the number of pulses per minute, and can be attributed to the number of droplets of the adipose tissue (exiting the reinjection cannula) per minute. It is appreciated, therefore, that in one embodiment the system 100 of the invention is configured to ensure that the harvesting pump 104 continually (that is, without interruptions in time) supplies the adipose tissue harvested from the site 116 to the input end of the tubing 118 while the reinjection pump 108 is causing this adipose tissue to be deposited at the injection location in a pulsed fashion (that is, in a fashion that is marked by interrupted extension in time and/or sequence), in the form of droplets or chunks or agglomerates.

It is recognized that the amount or degree of operation of the pump (in case of the peristaltic pump—the amount of rotation) during each single pulse affects the size of each droplet. Referring again to FIG. 4, a higher speed of rotation corresponds to the roller's rotation at a larger angle during each pulse, thereby defining a larger volume of fluid pushed along the tubing 118 towards the cannula 110 with each pulse. This type of flow distribution is important to maximize vascularization to the deposited adipose tissue, which has been demonstrated empirically. Distributing the agglomerates of adipose tissue by spacing them out at the recipient (reinjection) site provides each agglomerate with the increased chance of finding a blood supply.

Figure 13:
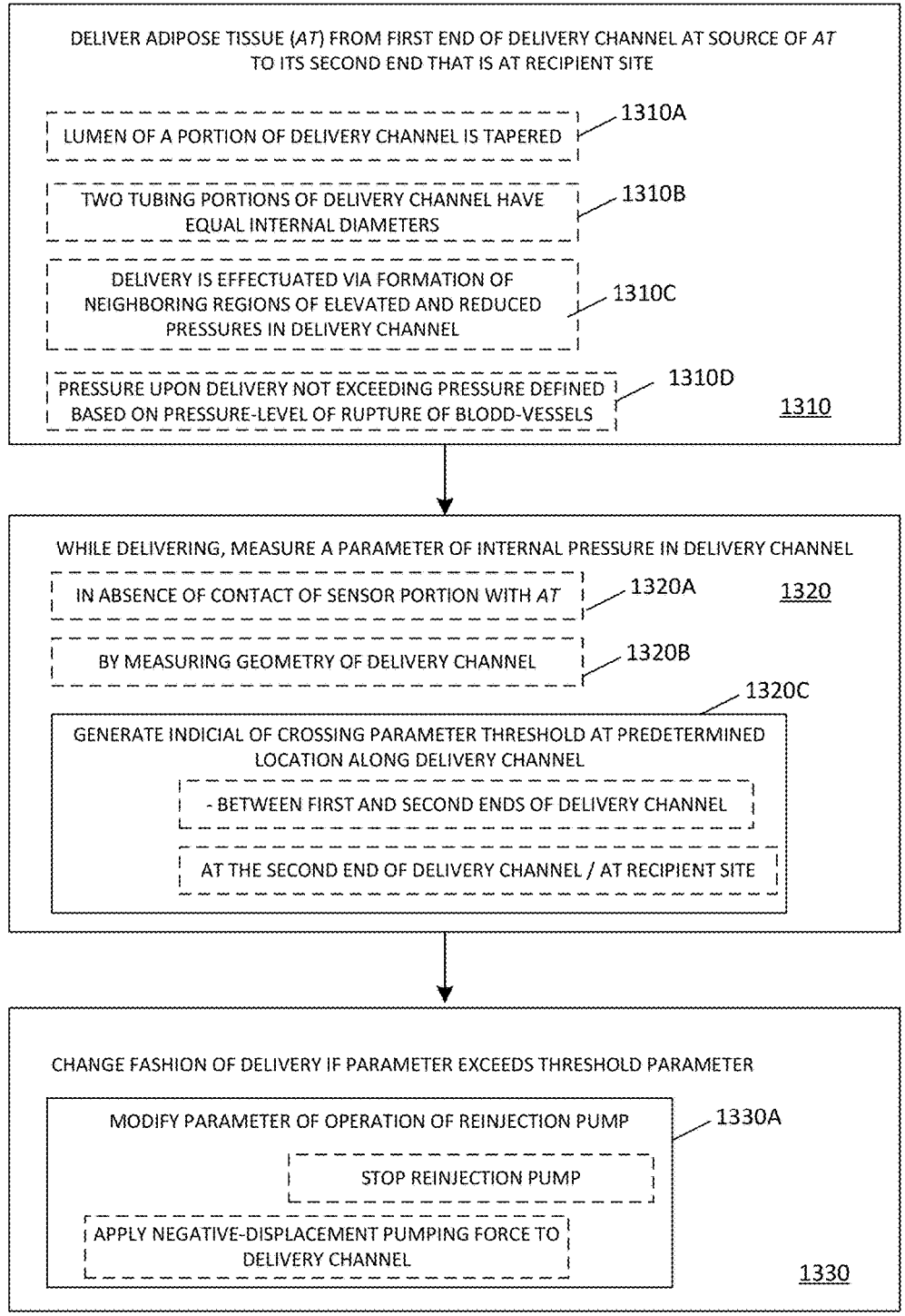
FIG. 13 is a flow-chart illustrating an embodiment of the method of the invention.

FIG. 13 provides a flow-chart illustrating a process of handling the adipose tissue according to an embodiment of the invention. At a step 1310, the AT is being delivered along the delivery channel from the source of AT to the recipient site (those two being fluidly connected with a delivery channel) and, while being so delivered, the internal pressure created by the AT in the delivery channel is being measured, 1320. The process of delivery can include the delivery through a lumen the internal diameter of which changes along the length of the lumen, for example a taper, 1310A; and/or along first and second tubes that, in a specific case, have substantially equal diameters, 1310B. In a specific case, the delivery is effectuated as a result of the pumping action caused by fluid interaction between two zones with respectively reduced and heightened pressure inside the delivery channel, 1310C. In another specific case, the absolute value of pressure under which the AT is being delivered to the recipient site does not exceed the absolute value of pressure judiciously defined with respect to the pressure level causing rupture of a wall of a blood-vessel at the recipient site, 1310D. Here, such absolute value of pressure can be defined in one embodiment as pressure causing rupture of the blood-vessel's wall; in a related embodiment—as pressure not exceeding the modulus of the practical aspiration pressure level by about 1.21 atmosphere (and, in practice, by as little as about 0.13 atmosphere and as much as about 3.3 atmosphere, preferably, by as little as about 1.21 atmosphere and as much as about 1.8 atmosphere). In another related embodiment, such absolute value of pressure is defined as the modulus of the practical aspiration pressure level. Notably, the absolute value of pressure is substantially all cases is dependent on the nature and/or location of the recipient site in a human body.

The pressure measurement process 1320 can be carried out such that no portion of the pressure-sensing unit or element in in direct contact with the AT, 1320A; and/or via measuring the geometrical characteristics of a portion of the delivery channel 1320B; and/or result in generating an output representing an occurrence of crossing the allowed pressure threshold (which is predetermined depending on the type of the recipient site, as discussed above), 1320C, as a result of which the transfer system is immediately modifying the procedure of the AT delivery, 1330. The modification of the process of the AT delivery can include the immediate rescission of the operation of the reinjection pump and/or reversing the pumping action at least until the measured pressure inside the delivery channel reaches the substantially zero level, 1330A.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention. In this disclosure, embodiments have been described in a way that enables a clear and concise specification to be written, but it is intended and will be appreciated that elements/components of related embodiments may be variously combined or separated without parting from the scope of the invention. In particular, it will be appreciated that all features described herein are applicable to all aspects of the invention.

In addition, it is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated generally falls under and may vary within a numerical range defined by an experimental measurement error that is typical when using a measurement method accepted in the art for such purposes.

Notably—whether explicitly illustrated in the drawings or not—an embodiment of the reinjection system of the invention includes electronic circuitry (for example, a computer processor) controlled by instructions stored in a memory, to perform specific data collection/processing and calculation steps as disclosed above. The memory may be random access memory (RAM), read-only memory (ROM), flash memory or any other memory, or combination thereof, suitable for storing control software or other instructions and data. Those skilled in the art should would readily appreciate that instructions or programs defining the operation of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement a method of the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

The invention as recited in claims appended to this disclosure is intended to be assessed in light of the disclosure as a whole, including features disclosed in prior art to which reference is made.

Various changes in the details, steps and components that have been described may be made by those skilled in the art within the principles and scope of the invention. For example, the implementation of the real-time control and adjustment of the internal pressure of the adipose tissue during the process of transfer of such tissue through the system can be employed with a syringe-based system with or without the syringe pump (while, for example, affixing the pressure sensor to the tubing transferring the fatty fluid from the syringe to the recipient location to instantaneously measure the pressure as discussed above or via measuring the increase in resistance to the movement of the syringe plunger, and to block the transfer channel from passing the adipose tissue once the pressure exceeds the pre-determined threshold level).

Disclosed aspects, or portions of these aspects, may be combined in ways not listed above. Accordingly, the invention should not be viewed as being limited to the disclosed embodiment(s).

The invention claimed is:

1. A method for handling of adipose tissue (AT) during transfer from a source of the AT to a recipient site, the method comprising:

channeling the AT within a hollow of a delivery channel of an AT transfer system from a first end of the delivery channel to a second end of the delivery channel, the second end being placed at the recipient site;

during said channeling, measuring at least one of (i) internal pressure formed by the AT within the hollow and (ii) a change in said internal pressure; and modifying a parameter of said channeling once said internal pressure exceeds a pre-determined threshold that is defined based at least in part on a pressure level causing rupture of a wall of a blood-vessel at the recipient site, wherein the source of the AT includes a biological tissue.

2. The method according to claim 1, wherein the pre-determined threshold is substantially equal to pressure exceeding a modulus of a practical aspiration pressure by no more than 1.21 atmosphere.

3. The method according to claim 1, wherein the pre-determined threshold is defined within a range from a first pressure level to a second pressure level, the first pressure level exceeding a modulus of a practical aspiration pressure by no less than 0.13 atmosphere, the second pressure level exceeding the practical aspiration pressure by no more than 3.3 atmosphere.

4. The method according to claim 1, wherein the pre-determined threshold is defined within a range from a first pressure level to a second pressure level, the first pressure level exceeding a modulus of a practical aspiration pressure by no less than 1.21 atmosphere, the second pressure level exceeding the practical aspiration pressure by no more than 1.8 atmosphere.

5. The method according to claim 1, wherein the pre-determined pressure level is defined depending on a location of the recipient site in a human body.

6. The method according to claim 1, wherein at least one of the following is satisfied:
   (a) wherein the channeling includes transferring the AT through a first flexible tube having a first inner diameter and through a second flexible tube having a second inner diameter, the first and second diameters being substantially equal; and
   (b) wherein said channeling includes forming a first area of first internal pressure and a second area of second internal pressure in the hollow, the first internal pressure being higher than internal pressure present in the hollow at the first end, the second internal pressure being lower than the internal pressure present in the hollow at the second end.

7. The method according to claim 1, further comprising conveying the AT through an aspiration cannula of the AT transfer system under first pressure;

wherein the channeling includes channeling the AT under second pressure, a modulus of a value of the second pressure not exceeding the pre-determined threshold.

8. The method according to claim 1, wherein at least one of the following conditions is satisfied:
   (i) said measuring is devoid of establishing physical contact between a component of a pressure sensor and the AT being channeled within the hollow;
   (ii) said measuring includes generating an electrical signal in response to a change of a geometrical parameter of the delivery channel, said change caused by the change of the internal pressure;
   (iii) said measuring includes generating indicia of said internal pressure exceeding the pre-determined threshold at a location of a first side-wall opening of a reinjection cannula of the AT transfer system, the reinjection cannula having been inserted into the recipient site.

9. The method according to claim 8, wherein said indicia includes an electrical signal, and wherein said modifying includes modifying a parameter of operation of a reinjection pump of the AT transfer system, the reinjection pump being operably attached to said delivery channel.

10. The method according to claim 1, wherein said modifying includes at least one of (i) stopping a motor of a reinjection pump of the AT transfer system, and (ii) reversing a direction of AT pumping until the internal pressure is reduced to substantially zero.

11. The method according to claim 1, wherein at least one of the following conditions is satisfied:
   (a) wherein the first end includes a side-wall opening of an aspiration cannula of the AT transfer system, the second ends includes a side-wall opening of a reinjection cannula of the AT transfer system, and
   wherein said channeling includes extracting the AT from an aspiration site and collecting the AT in a container that is in fluid communication with both the aspiration and reinjection cannulae; and
   (b) the method further comprising at least one of the following:
      (i) injecting the AT through the second end into the recipient site in a pulsed fashion; and
      (ii) injecting the AT into the recipient site through a first side-wall opening of a reinjection cannula of the system while the AT is being harvested from an aspiration site through a second side-wall opening of an aspiration cannula of the AT transfer system,
      wherein the aspiration cannula and the reinjection cannula are uninterruptingly fluidly connected with one another during said channeling.

12. A system configured to deliver an adipose tissue to a recipient site, the system comprising:

a biocompatible flexible tubing with a first end and a second end, wherein the first end is dimensioned to receive said adipose tissue that has been received from a source location, and the second end in operation is fluidly connected to a location of the recipient site;

a first pump attached to the flexible tubing to cause movement of the adipose tissue through the flexible tubing from the first end to the second end;

a pressure sensor operably connected to at least one of the first pump and the biocompatible flexible tubing to measure an internal pressure of the adipose tissue upon its propagating through the biocompatible flexible tubing; and a reinjection cannula fluidly connected to the second end, wherein said pressure sensor is configured to cause the system to interrupt a process of propagation of the adipose tissue through the biocompatible flexible tubing to prevent fat embolism at the recipient site when pressure of the adipose tissue at a side-wall opening of the reinjection cannula exceeds a predetermined amount, wherein the predetermined amount is dependent on the location of the recipient site in a human body while, at the same time, the predetermined amount is defined based at least in part on a pressure level causing rupture of a wall of a blood-vessel at the recipient site.

13. The system according to claim 12, wherein the pre-determined amount is defined within a range of pressure levels from a first pressure level to a second pressure level, wherein the first pressure level exceeds a modulus of a practical aspiration pressure by no less than 0.13 atmosphere and the second pressure level exceeds the practical aspiration pressure by no more than 3.3 atmosphere.

14. The system according to claim 12, wherein said pressure sensor is configured to cause the system to interrupt the process of propagation of the adipose tissue through the biocompatible flexible tubing when pressure of the adipose tissue at the side-wall opening of the reinjection cannula exceeds a modulus of practical aspiration pressure by more than 1.21 atmosphere.

15. The system according to claim 12, wherein the pre-determined amount is defined within a range of pressure levels from a first pressure level to a second pressure level, wherein the first pressure level exceeds a modulus of a practical aspiration pressure by no less than 1.21 atmosphere and the second pressure level exceeds the practical aspiration pressure by no more than 1.8 atmosphere.

16. The system of claim 12, wherein at least one of the following conditions is satisfied: (a) the first pump is devoid of a portion that, in operation, contacts the adipose tissue in the biocompatible flexible tubing, and (b) the pressure sensor is devoid of a portion that, in operation, contacts the adipose tissue.

17. The system of claim 12, wherein at least one of the following is satisfied:
 (i) the biocompatible flexible tubing is configured to have, in absence of external force applied to said biocompatible flexible tubing, a substantially constant internal diameter at any point between the first and second ends;
 (ii) the first pump includes a first pump controller configured to operate the first pump in a pulsed regime to cause the adipose tissue move in a pulsed fashion from the first end to the second end;
 (iii) the pressure sensor includes a transducer configured to measure said internal pressure by measuring a change of a parameter of the biocompatible flexible tubing caused by changes in said internal pressure; and
 (iv) the first pump is devoid of a movable part that is internal to said biocompatible flexible tubing.

18. The system of claim 12, further comprising
 an aspiration cannula; and
 a volume fillable, during an operation of the system, with said adipose tissue, wherein the volume is disposed in fluid communication between the aspiration cannula and said biocompatible flexible tubing.

19. A system configured to deliver an adipose tissue to a recipient site, the system comprising:
 a storage volume containing the adipose tissue;
 a hollow delivery channel with first and second ends, the first end fluidly connected with the storage volume, the second end fluidly connected with a location of the recipient site;
 a first pump configured to apply a positive-displacement pumping force to the delivery channel to cause a movement of the adipose tissue from the first end to the location of the recipient site; and
 a pressure sensor attached externally to a component of the system, the sensor configured to measure an internal pressure of the adipose tissue in the delivery channel and generate an output signal representative of said internal pressure;
 a programmable processor operably connected to the pressure sensor and configured to modify an operation of the first pump, to prevent fat embolism at the recipient site, in response to a value of the output signal being in a pre-determined relationship with a threshold value, wherein the threshold value is dependent on the location of the recipient site while, at the same time, the threshold value represents pressure defined based at least in part on a pressure level causing rupture of a wall of a blood-vessel at the recipient site.

20. The system according to claim 19, wherein the threshold value represents pressure defined within a range of pressure levels from a first pressure level to a second pressure level, wherein the first pressure level exceeds a modulus of a practical aspiration pressure by no less than 0.13 atmosphere and the second pressure level exceeds the practical aspiration pressure by no more than 3.3 atmosphere.

* * * * *